US011142548B2

(12) United States Patent
Sennlaub et al.

(10) Patent No.: US 11,142,548 B2
(45) Date of Patent: Oct. 12, 2021

(54) AGENTS THAT ACTIVATE CD47 AND THEIR USE IN THE TREATMENT OF INFLAMMATION

(71) Applicants: SORBONNE UNIVERSITE, Paris (FR); CENTRE NATIONAL DE LA RECHERCHE SCIENTIFIQUE, Paris (FR); INSERM (INSTITUT NATIONAL DE LA SANTÉ ET DE LA RECHERCHE MÉDICALE), Paris (FR)

(72) Inventors: Florian Sennlaub, Paris (FR); Michael Housset, Québec (CA); Xavier Guillonneau, Boulogne Billancourt (FR); José-Alain Sahel, Paris (FR); Philippe Karoyan, Courson-Monteloup (FR)

(73) Assignees: SORBONNE UNIVERSITE, Paris (FR); CENTRE NATIONAL DE LA RECHERCHE SCIENTIFIQUE, Paris (FR); INSERM (INSTITUT NATIONAL DE LA SANTÉ ET DE LA RECHERCHE MÉDICALE), Paris (FR)

( * ) Notice: Subject to any disclaimer, the term of this patent is extended or adjusted under 35 U.S.C. 154(b) by 158 days.

(21) Appl. No.: 16/300,438

(22) PCT Filed: May 10, 2017

(86) PCT No.: PCT/EP2017/061151
§ 371 (c)(1),
(2) Date: Nov. 9, 2018

(87) PCT Pub. No.: WO2017/194586
PCT Pub. Date: Nov. 16, 2017

(65) Prior Publication Data
US 2019/0225649 A1 Jul. 25, 2019

(30) Foreign Application Priority Data

May 10, 2016 (EP) ..................................... 16169072
Feb. 2, 2017 (EP) ..................................... 17154452

(51) Int. Cl.
*A61K 38/00* (2006.01)
*C07K 7/08* (2006.01)
*A61K 38/16* (2006.01)
*A61P 27/02* (2006.01)
*A61P 29/00* (2006.01)

(52) U.S. Cl.
CPC ................ *C07K 7/08* (2013.01); *A61K 38/16* (2013.01); *A61P 27/02* (2018.01); *A61P 29/00* (2018.01)

(58) Field of Classification Search
None
See application file for complete search history.

(56) References Cited

U.S. PATENT DOCUMENTS

| 4,816,567 | A | 3/1989 | Cabilly et al. |
| 5,591,828 | A | 1/1997 | Bosslet et al. |
| 6,001,962 | A | 12/1999 | Ramer et al. |
| 6,846,637 | B1 | 1/2005 | Chiodi |
| 7,867,727 | B2 | 1/2011 | Hageman |
| 9,017,675 | B2 | 4/2015 | Liu et al. |
| 9,382,320 | B2 | 7/2016 | Liu et al. |
| 10,004,780 | B2 | 6/2018 | Leveillard et al. |
| 10,513,503 | B2 * | 12/2019 | Fontaine .................. A61P 27/02 |
| 10,519,232 | B2 * | 12/2019 | Sennlaub ................ A61P 43/00 |
| 2006/0063715 | A1 | 3/2006 | Whitlow et al. |
| 2011/0237498 | A1 * | 9/2011 | Raymond ................ A61P 43/00 514/1.7 |
| 2011/0269807 | A1 | 11/2011 | Baciu |
| 2012/0040884 | A1 | 2/2012 | Hageman |
| 2014/0127269 | A1 * | 5/2014 | Masli ..................... C07K 14/78 424/400 |
| 2015/0050646 | A1 | 2/2015 | Hageman |
| 2016/0304609 | A1 | 10/2016 | Liu et al. |

FOREIGN PATENT DOCUMENTS

| EP | 0 404 097 A2 | 12/1990 | |
| WO | 93/11161 A1 | 6/1993 | |
| WO | 99/40940 A1 | 8/1999 | |
| WO | 2008/008986 A2 | 1/2008 | |
| WO | 2010/070047 A1 | 6/2010 | |
| WO | WO-2010070047 A1 * | 6/2010 | ......... C07K 14/4703 |
| WO | 2011/137363 A1 | 11/2011 | |
| WO | 2011/143624 A2 | 11/2011 | |
| WO | 2013/182650 A1 | 12/2013 | |
| WO | 2014/060517 A1 | 4/2014 | |

OTHER PUBLICATIONS

Levy, et al., EMBO Molecular Medicine, Feb. 2015, p. 211-226, vol. 7 No. 2 (Year: 2015).*
An et al., "Identification of Novel Substrates for the Serine Protease HTRA1 in the Human RPE Secretome", Investigative Ophthalmology & Visual Science, Jul. 2010, p. 3379-3386, vol. 51 No. 7.
Barclay, "Signal regulatory protein alpha (SIRPα)/CD47 interaction and function", Curr Opin Immunol., Feb. 2009, p. 47-52, vol. 21 No. 1.
Caspi, "Th1 and Th2 responses in pathogenesis and regulation of experimental autoimmune uveoretinitis", International Reviews of Immunology, Mar.-Jun. 2002, p. 197-208, vol. 21 No. 2-3.
Chao et al., "The CD47-SIRPα Pathway in Cancer Immune Evasion and Potential Therapeutic Implications", Curr Opin Immunol. Apr. 2012, p. 225-232, vol. 24 No. 2.
Chen et al., "Persistent Inflammation Subverts Thrombospondin-1-Induced Regulation of Retinal Angiogenesis and Is Driven by CCR2 Ligation", The American Journal of Pathology, Jan. 2012, p. 235-245, vol. 180 No. 1.

(Continued)

*Primary Examiner* — Satyanarayana R Gudibande
(74) *Attorney, Agent, or Firm* — Nixon & Vanderhye

(57) ABSTRACT

Disclosed are agents activating CD47 and their use in the treatment of inflammation, in particular non-resolving low grade inflammation, characterized by chronic MP infiltration, such as age-related macular degeneration. Also disclosed are pharmaceutical compositions, medicaments and kits including the agents.

5 Claims, 6 Drawing Sheets

Specification includes a Sequence Listing.

(56) References Cited

OTHER PUBLICATIONS

Combadière et al., "CX3CR1-dependent subretinal microglia cell accumulation is associated with cardinal features of age-related macular degeneration", The Journal of Clinical Investigation, Oct. 2007, p. 2920-2928, vol. 117 No. 10.

Cruz-Guilloty et al., "Infiltration of Proinflammatory M1 Macrophages into the Outer Retina Precedes Damage in a Mouse Model of Age-Related Macular Degeneration", International Journal of Inflammation, 2013, vol. 2013 Article No. 503725.

DeWan et al., "HTRA1 Promoter Polymorphism in Wet Age-Related Macular Degeneration", Science, Nov. 10, 2006, p. 989-992, vol. 314.

Edwards et al., "Complement Factor H Polymorphism and Age-Related Macular Degeneration", Science, Apr. 15, 2005, p. 421-424, vol. 308 (5720).

Gagnon et al., "Leukotrienes and macrophage activation: augmented cytotoxic activity and enhanced interleukin 1, tumor necrosis factor and hydrogen peroxide production", Agents Actions, Jan. 1989, p. 141-147, vol. 26 (1-2).

Gautier et al., "Local apoptosis mediates clearance of macrophages from resolving inflammation in mice", Blood, Oct. 10, 2013, p. 2714-2722, vol. 122 No. 15.

Gilroy et al., "Inducible cyclooxygenase may have anti-inflammatory properties", Nature Medicine, Jun. 1999, p. 698-701, vol. 5 No. 6.

Glass et al., "Mechanisms Underlying Inflammation in Neurodegeneration", Cell, Mar. 19, 2010, p. 918-934, vol. 140 No. 6.

Grivennikov et al., "Immunity, Inflammation, and Cancer", Cell, Mar. 19, 2010, p. 883-899, vol. 140 No. 6.

Gupta et al., "Activated microglia in human retinitis pigmentosa, late-onset retinal degeneration, and age-related macular degeneration", Experimental Eye Research, Apr. 2003, p. 463-471, vol. 76 No. 4.

Haines et al., "Complement Factor H Variant Increases the Risk of Age-Related Macular Degeneration", Science, Apr. 15, 2005, p. 419-421, vol. 308.

Hotamisligil, "Endoplasmic Reticulum Stress and the Inflammatory Basis of Metabolic Disease", Cell, Mar. 19, 2010, p. 900-917, vol. 140 No. 6.

Hou et al., "Lipopolysaccharide Increases the Incidence of Collagen-Induced Arthritis in Mice Through Induction of Protease HTRA-1 Expression", Arthritis & Rheumatism, Nov. 2013, p. 2835-2846, vol. 65 No. 11.

Kerr et al., "The dynamics of leukocyte infiltration in experimental autoimmune uveoretinitis", Progress in Retinal and Eye Research, Sep. 2008, p. 527-535, vol. 27 No. 5.

Klein et al., "The Epidemiology of Age-Related Macular Degeneration", Am J Ophthalmol, Mar. 2004, p. 486-495, vol. 137 No. 3.

Levy et al., "Apolipoprotein E promotes subretinal mononuclear phagocyte survival and chronic inflammation in age-related macular degeneration", EMBO Molecular Medicine, Feb. 2015, p. 211-226, vol. 7 No. 2.

Lim et al., "Glucocorticoids exert opposing effects on macrophage function dependent on their concentration", Immunology, Sep. 2007, p. 47-53, vol. 122 No. 1.

Liu et al., "A practical guide to the monitoring and management of the complications of systemic corticosteroid therapy", Allergy, Asthma & Clinical Immunology, Aug. 15, 2013, vol. 9 No. 1.

Manna et al., "CD47 augments Fas/CD95-mediated Apoptosis", The Journal of Biological Chemistry, Aug. 19, 2005, p. 29637-29644, vol. 280 No. 33.

Nathan and Ding, "Nonresolving inflammation", Cell, Mar. 19, 2010, p. 871-882, vol. 140 No. 6.

Ng et al., "Thrombospondin-1-Mediated Regulation of Microglia Activation after Retinal Injury", Investigative Ophthalmology & Visual Science, Nov. 2009, p. 5472-5478, vol. 50 No. 11.

Pettersen et al., "CD47 Signals T Cell Death", The Journal of Immunology, Jun. 15, 1999, p. 7031-7040, vol. 162, No. 12.

Seddon et al., "Dietary Carotenoids, Vitamins A, C, and E, and Advanced Age-Related Macular Degeneration", JAMA, Nov. 9, 1994, p. 1413-1420, vol. 272 No. 18.

Sennlaub et al., "CCR2(+) monocytes infiltrate atrophic lesions in age-related macular disease and mediate photoreceptor degeneration in experimental subretinal inflammation in Cx3cr1 deficient mice", EMBO Molecular Medicine, Nov. 2013, p. 1775-1793, vol. 5 No. 11.

Streilein et al., "Immunobiology and privilege of neuronal retina and pigment epithelium transplants", Vision Research, Feb. 2002, p. 487-495, vol. 42 No. 4.

Tedesco and Haragsim, "Cyclosporine: A Review", Journal of Transplantation, 2012, 2012:230386.

Tsutsumi et al., "The critical role of ocular-infiltrating macrophages in the development of choroidal neovascularization", Journal of Leukocyte Biology, Jul. 2003, p. 25-32, vol. 74 No. 1.

Uno et al., "Antitumor activity of a monoclonal antibody against CD47 in xenograft models of human leukemia", Oncology Reports, May 2007, p. 1189-1194, vol. 17 No. 5.

Wang et al., "Lack of Thrombospondin-1 and Exacerbation of Choroidal Neovascularization", Arch Ophthalmol, May 1, 2012, p. 615-620, vol. 130 No. 5.

Yang et al., "A variant of the HTRA1 Gene Increases Susceptibility to Age-Related Macular Degeneration", Science, Nov. 10, 2006, p. 992-993, vol. 314(5801).

Armant et al., "CD47 Ligation Selectively Downregulates Human Interleukin 12 Production", The Journal of Experimental Medicine, 1999, pp. 1175-1181, vol. 190, No. 8.

International Search Report, dated Aug. 1, 2017, from corresponding PCT application No. PCT/EP2017/061151.

* cited by examiner

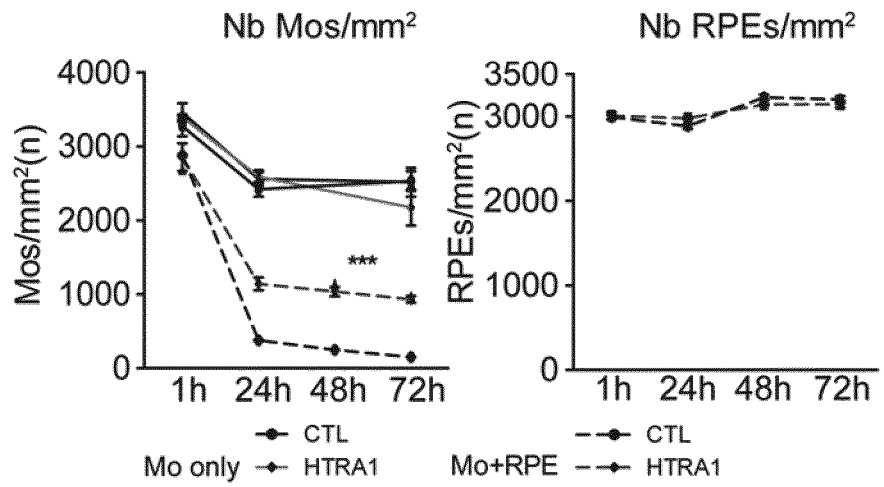
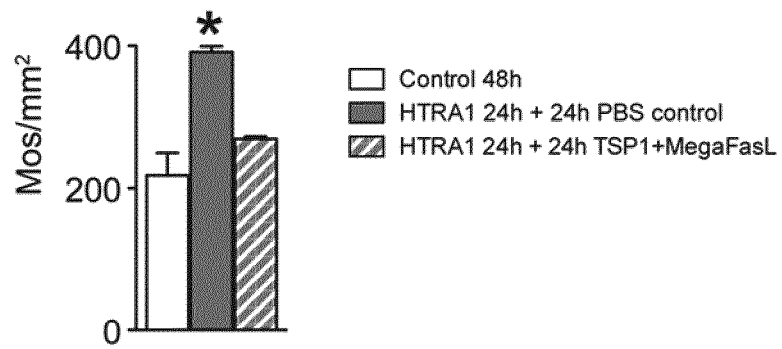
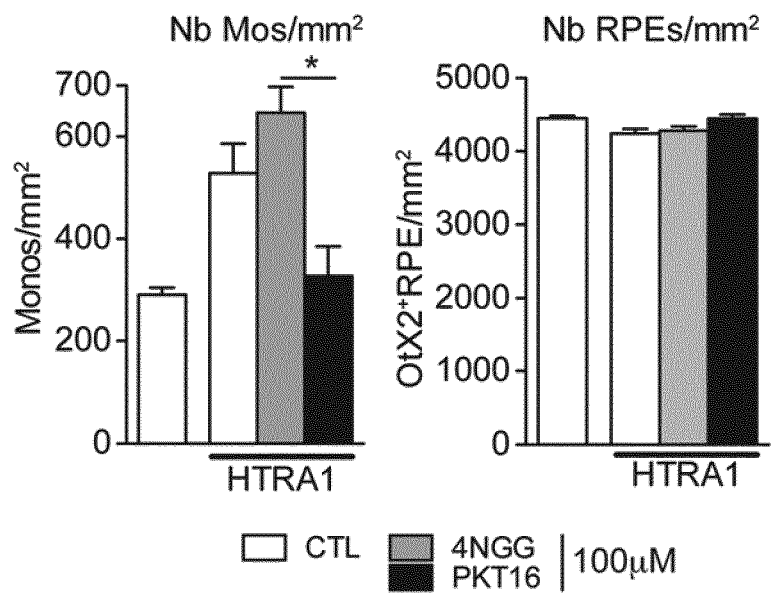
FIG. 4A-C

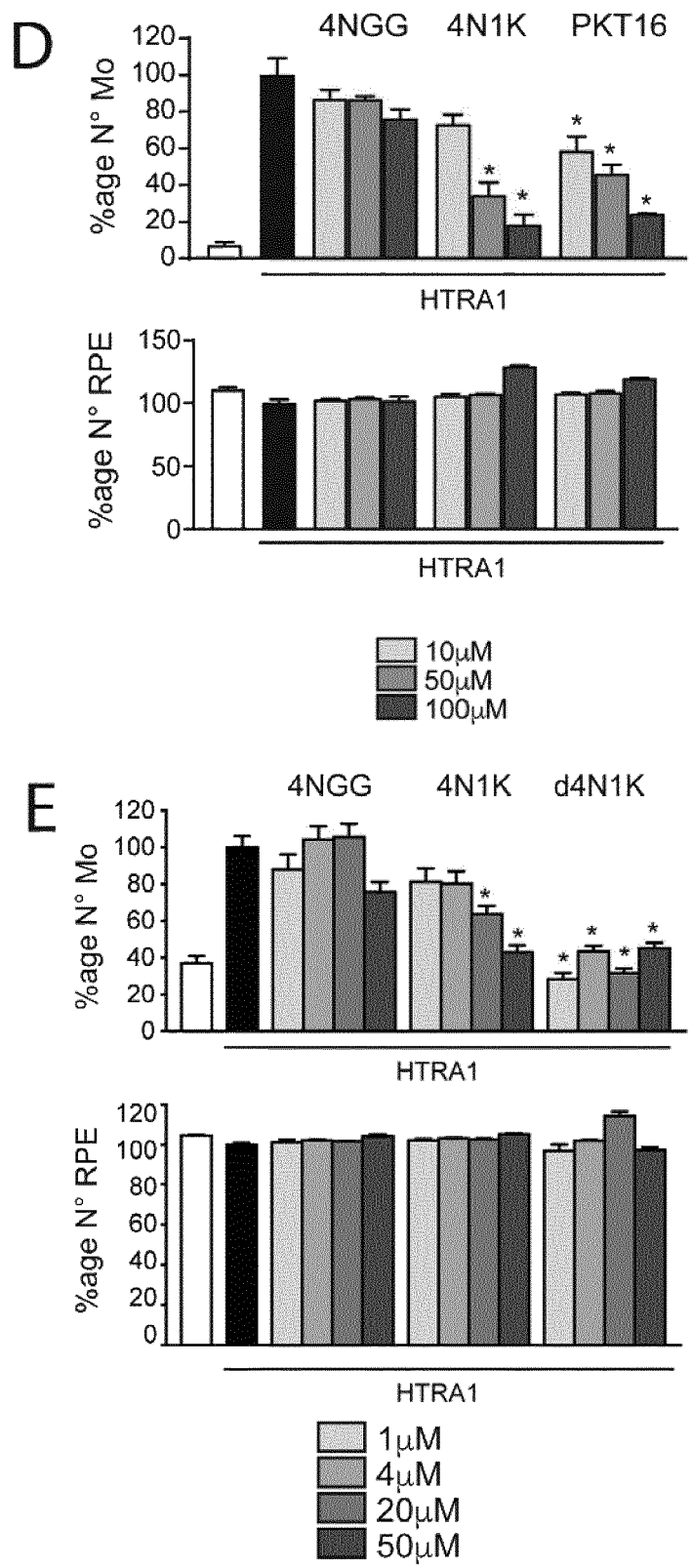
FIG. 4D-E

AGENTS THAT ACTIVATE CD47 AND THEIR USE IN THE TREATMENT OF INFLAMMATION

FIELD OF INVENTION

The present invention relates to agents that activate CD47. The present invention also relates to the treatment of inflammatory disorders and diseases, such as age related macular degeneration.

BACKGROUND OF INVENTION

Age related macular degeneration (AMD) is the leading cause of legal blindness in the developed world. There are two clinical forms of late AMD: the fast developing exudative form ("wet" AMD) defined by choroidal neovascularisation (CNV) and the more slow developing atrophic form characterized by retinal pigment epithelium (RPE) atrophy and the photoreceptor degeneration known as geographic atrophy (GA, or late stage "dry" AMD). Although AMD is often classified into 'atrophic' and 'wet' forms, they both develop on a background of increased innate immunity activation and are associated with the same polymorphisms such as those of Complement Factor-H (CFH) (Haines et al., Science. 2005; 308:419-421; Edwards et al., Science. 2005, 308:421-424), Serine Protease High Temperature Requirement A1 (HTAR1) and Age-Related Maculopathy Susceptibility 2 (ARMSD2) (Dewan et al., Science. 2006, 314:989-992; Yang et al., Science. 2006, 314:992-993).

Mononuclear phagocytes (MP) comprise a family of cells that include microglial cells (MC), monocytes (Mo), and macrophages (Mφ). Physiologically, MCs are present only in the inner retina. The subretinal space, located between the retinal pigment epithelium (RPE) and the photoreceptor outer segments (POS), is a zone of immune privilege mediated by immunosuppressive RPE signals, including leukocyte suppressing FasL (CD95L). Nevertheless, MPs accumulate in the subretinal space in the two advanced forms of sight-threatening AMD (Klein et al., Am J Ophthalmol. 2004, 137:486-495). They are in close contact with the RPE in choroidal neovascularisation and in the vicinity of the RPE lesion in geographic atrophy (Gupta et al., Exp Eye Res. 2003, 76:463-471; Sennlaub et al., EMBO Mol Med. 2013, 5:1775-1793). MPs are thought to contribute to CNV (Tsutsumi et al., J Leukoc Biol. 2003, 74:25-32) and to photoreceptor degeneration in GA (Cruz-Guilloty et al., Int J inflam. 2013, 2013:503725). It was recently showed that subretinal MPs are also present in and around soft drusen, that are an important risk factor to develop late AMD (Sennlaub et al., EMBO Mol Med. 2013, 5:1775-1793; Levy et al., EMBO Mol Med. 2015, 7:211-226). Nevertheless, the reasons for the alteration of subretinal immunosuppression and subsequent accumulation of MPs in AMD remain unknown.

There are known treatments for wet AMD, such as the use of anti-neovascular agents and photodynamic therapy (laser irradiation of the macula). Anti-neovascular agents for treatment of wet AMD include agents which block the action of vascular endothelial growth factor (VEGF) thereby slowing angiogenesis (formation of new blood vessels in the retina) which leads to choroidal neovascularization and loss of vision in wet AMD patients. Such "anti-VEGF" agents approved or in clinical study for treating wet AMD include bevacizumab (AVASTIN™), ranibizumab (LUCENTIS™), and aflibercept (EYLEA™). New proposals of treatments are described, for example, in WO2008008986, which discloses the administration of CFHR1 and/or CFHR3 polypeptide. The international patent application WO2011137363 is directed to the reduction of 5-lipoxygenase (5-LO) activity to treat age-related macular degeneration. Another example is WO2014060517 which concerns the administration of a RdCVFL polynucleotide or polypeptide to a subject to treat AMD.

However, no drug is currently on the market for treating dry AMD or geographic atrophy, although vitamin supplements with high doses of antioxidants, lutein and zeaxanthin, have been suggested to slow the progression (Seddon et al., Eye Disease Case-Control Study Group JAMA. 1994, 272:1413-1420). Therapeutics such as glucocorticoids, non-steroidal anti-inflammatory drugs (NSAID) such as cyclooxygenase inhibitors, and immunosuppressants such as ciclosporin are often referred to as "anti-inflammatory" drugs, because they inhibit different aspects of inflammation. However, they do not inhibit inflammation as a whole. Ciclosporin inhibits calcinurin-induced transcription of cytokine genes mainly in activated T cells (Matsuda and Koyasu, 2000) which impacts the function of lymphocytes, but it also upregulates toll-like receptors on Mφs (Ciclosporin) (Tedesco and Haragsim, Journal of Transplantation. 2012, volume 2012, 230386). Glucocorticoids affect carbohydrate, fat, and protein metabolism, and are possibly best known for their ability to repress delayed hypersensitivity reactions by a direct action on T cells (Liu et al., Allergy Asthma Clin Immunol. 2013, 9:30), but exert opposing effects on Mφ function depending on their concentration (Lim et al., Immunology. 2007, 122:47-53), NSAID are cyclooxygenase inhibitors that inhibit the production of prostaglandins, but increase the synthesis of leukotriens (Robinson, Clin Exp Rheumatol. 1989, 7 Suppl 3:S155-161) that activate MPs (Gagnon et al., Agents Actions. 1989.26: 141-147) and can prolong MP infiltration (Gilroy et al., Nat Med. 1999, 5:698-701). This lack of efficiency to inhibit MP-mediated subretinal inflammation might also explain why widely used "anti-inflammatory" therapies, such as treatments with systemic NSAIDs, have not slowed AMD progression.

Together, these considerations show the need for a specifically adapted "anti-inflammatory" therapy to inhibit the mechanisms of subretinal MP accumulation and their activation in AMD.

AMD is associated with non-resolving and low-grade chronic inflammation that mainly involves the innate immune system and most notably the accumulation of MPs (Combadiere et al., J Clin Invest. 2007, 117:2920-2928; :Levy et al., EMBO Mol Med. 2015, 7:211-226). Contrary to fast evolving autoimmune lesions, characterized by cytotoxic T lymphocytes, neutrophils and MPs (Carpi, International reviews of immunology. 2002, 21:197-208; Kerr et al., Prog Retin Eye Res. 2008, 27:527-535), infiltrating leukocytes in slowly-evolving GA are predominantly MPs which is similar to other protracted age-related diseases including atherosclerosis, neurodegenerative diseases and cancer (Grivennikov et al., Cell. 2010, 140:883-899; Hotamisligil, Cell. 2010, 140:900-917). More generally, inflammation is the organism's response to tissue injury and microbial invasion. Ideally, it quickly and efficiently eliminates pathogens and repairs the tissue injury either by regeneration or scarring. If the inflammatory response is not quickly controlled, it can become pathogenic and contribute to disease progression, as seen in many chronic inflammatory diseases. Non-resolving and low-grade chronic inflammation is observed in contexts such as metabolic diseases (obesity, atherosclerosis) (Hotamisligil, Cell. 2010, 140:

900-917), neurodegenerative diseases (Glass et at., Cell. 2010, 140:918-934) and cancers (Grivennikov et al., Cell. 2010, 140:883-899), and therefore contributes significantly to the pathogenesis of many chronic, age-related diseases. Non-resolving inflammation is not a primary cause of these diseases, but it contributes significantly to their pathogenesis as microbicidal mediators produced by neutrophils and interstitial macrophages (reactive oxygen species, proteases and inflammatory cytokines . . . ) can also cause considerable collateral damages to host cells, which itself causes more inflammation. It is often not clear to what extent chronic inflammation persists because of a continuous primary problem or to the incapacity to exit the cycle of inflammation, collateral damage, and renewed inflammation. In the affected tissues, it is often associated with persistence of mononuclear phagocytes (MP), a family of cells that include monocyte (Mo), resident macrophages (rMφ) such as microglial cells (MC), and monocyte-derived inflammatory macrophages (iMφ) that arise during inflammation, but little with lymphocyte infiltration or an adaptive immune response (Nathan and Ding, Cell. 2010, 140:871-882).

In view of these elements, there is therefore still an ongoing need for identifying active ingredients for preventing and/or treating non-resolving low grade inflammation, more specifically inflammation associated with mononuclear phagocytes accumulation, and more particularly AMD.

This objective is reached by the present invention, since the inventors have surprisingly demonstrated that TSP1 mediates mononuclear phagocytes elimination via its receptor CD47.

CD47 is known to play a key role in immune and angiogenic responses. In particular, binding of TSP-1 to CD47 influences several fundamental cellular functions including cell migration and adhesion, cell proliferation or apoptosis, and plays a role in the regulation of angiogenesis and lymphocyte elimination (Chao et al., Curr. Opin. immunol. 2012, 24 (2):225-32). CD47 also interacts with signal-regulatory protein alpha (SIRPα), an inhibitory transmembrane receptor present on myeloid cells. The CD47/SIRPα interaction leads to bidirectional signaling, resulting in different cell-to-cell responses including inhibition of phagocytosis, stimulation of cell-cell fusion, and T-cell activation (Barclay, Curr. Opin. Immunol. 2009, 21 (1): 47-52).

The international patent application WO99/40940 discloses the use of anti-CD47 antibodies for prevention or treatment of inflammatory diseases. Similarly, WO2010/70047 describes a CD47 binding polypeptide for use as a medicament in the treatment of autoimmune and inflammatory disorders. In another hand, WO2011/43624 discloses the use of anti-CD47 antibodies for modulating phagocytosis. However, treatment of inflammatory diseases according to these patent applications implies the inhibition of CD47.

Surprisingly, the Applicant demonstrated that activation of CD47 is crucial for mononuclear phagocytes elimination, and that CD47 activation is mediated by its ligand TSP1. Moreover, the inventors have shown that HTRA1 degrades TSP1, thereby inhibiting its activation of CD47 and mononuclear phagocytes elimination. Furthermore, inventors have surprisingly established that treatment with a CD47 agonist in combination with a Fas agonist results in restoring the HTRA1-induced mononuclear phagocytes accumulation and thereby treating the inflammation.

The present invention thus relates to an agent that activates CD47 and its use in the treatment of non-resolving MP accumulation and inflammation, such as age related macular degeneration.

SUMMARY

The present invention relates to an agent for use for treating inflammation, wherein said agent activates CD47.

In one embodiment, the agent for use for treating inflammation of the invention directly activates CD47. In one embodiment, said agent is a CD47 agonist, preferably a TSP1 peptidomimetic. In another embodiment, said agent is an activating peptide selected from the group comprising 4N1K, PKHB1 and PKT16.

In another embodiment, the agent for use for treating inflammation of the invention indirectly activates CD47. In one embodiment, said agent is selected from the group comprising TSP1 activators, HTRA1 inhibitors and Fas activators.

In one embodiment, the inflammation according to the invention is an acute or a chronic inflammation. In one embodiment, the agent is for use for treating non-resolving chronic inflammations, preferably non-resolving low-grade inflammations. In one embodiment, said inflammation is an inflammation associated with mononuclear phagocytes accumulation. In one embodiment, said inflammation is selected from the group comprising age-related macular degeneration; retinitis pigmentosa; neurodegenerative diseases, such as Parkinson's disease, multiple sclerosis or Alzheimer's disease; and metabolic disorders, such as obesity or atherosclerosis. In a particular embodiment, said inflammation is age-related macular degeneration.

The present invention further relates to a composition comprising at least one agent as described hereinabove. In one embodiment, the composition according to the invention comprises a CD47 agonist and a Fas activator.

Another object of the present invention is a pharmaceutical composition comprising at least one agent activating CD47 and at least one pharmaceutically acceptable carrier for use for treating inflammation, preferably age-related macular degeneration.

A further object of the present invention is a medicament comprising at least one agent activating CD47 for use for treating inflammation, preferably age-related macular degeneration.

In one embodiment, the agent, the pharmaceutical composition or the medicament as described hereinabove are administered intraocularly, preferably by intravitreal injection, or applied by topical ocular administration.

The present invention also relates to a kit comprising at least one agent, the pharmaceutical composition or the medicament as described hereinabove.

Definitions

In the present invention, the following terms have the following meanings:

The term "amino acid" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, in one embodiment, the term "amino acid" includes both D- and L-amino acids (stereoisomers).

The term "amino acid substitution" refers to the replacement in a polypeptide of one amino acid with another amino acid. In one embodiment, an amino acid is replaced with another amino acid having similar structural and/or chemical properties, e.g. conservative amino acid replacements, "Conservative amino acid substitution" may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; negatively charged (acidic) amino acids include aspartic acid and glutamic acid. Non-conservative substitutions will entail exchanging a member of one of these classes for another class. For example, amino acid substitutions can also result in replacing one amino acid with another amino acid having different structural and/or chemical properties, for example, replacing an amino acid from one group (e.g., polar) with another amino acid from a different group (e.g., basic). Amino acid substitutions can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful.

The term "identity" refers to a measure of the identity of nucleotide sequences or amino acid sequences. In general, the sequences are aligned so that the highest order match is obtained. "Identity" per se has an art-recognized meaning and can be calculated using published techniques. See, e.g.: Computational Molecular Biology, Lesk, A.M., ed., Oxford University Press, New York, 1988; Biocomputing: informatics And Genome Projects, Smith, D. W., ed., Academic Press, New York, 1993; Computer Analysis Of Sequence Data, Part 1, Griffin, A. M., and Griffin, H. G., eds, Humana Press, New Jersey, 1994; Sequence Analysis In Molecular Biology, von Heijne, G., Academic Press, 1987; and Sequence Analysis Primer, Gribskov, M. and Devereux, J., eds, M Stockton Press, New York, 1991. While there exist a number of methods to measure identity between two polynucleotide or polypeptide sequences, the term "identity" is well known to skilled artisans (Carillo and Lipton, SIAM J Applied Math, 1998, 48:1073). Methods commonly employed to determine identity or similarity between two sequences include, but are not limited to, those disclosed in Guide to Huge Computers, Martin J. Bishop, ed., Academic Press, San Diego, 1994; and Carillo and Lipton, SIAM J Applied Math, 1998, 48:1073. Methods to determine identity and similarity are codified in computer programs. Preferred computer program methods to determine identity and similarity between two sequences include, but are not limited to, GCG program package (Devereux et al., J Molec Biol, 1990, 215:403). Most preferably, the program used to determine identity levels was the GAP program, as was used in the Examples below.

As an illustration, by a polynucleotide having a nucleotide sequence having at least, for example, 95% "identity" to a reference nucleotide sequence is intended that the nucleotide sequence of the polynucleotide is identical to the reference sequence except that the polynucleotide sequence may include an average up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

The term "peptide" refers to a linear polymer of amino acids of less than 50 amino acids linked together by peptide bonds. The peptides of the invention are not limited to a specific length of the product. This term does not refer to or exclude post-expression modifications of the peptide, for example, glycosylation, acetylation, phosphorylation and the like, as well as other modifications known in the art, both naturally occurring and non-naturally occurring.

The term "peptide linker", also called "spacer peptide", refers to a peptide used to link 2 peptides or polypeptides together. In one embodiment, a peptide linker of the invention comprises from 3 to 50 amino acids. Peptide linkers are known in the art or are described herein. In one embodiment of the present invention, the peptide linker is also referred to as "L".

The term "polynucleotide" refers to any polyribonucleotide or polydeoxyribonucleotide, which may be unmodified RNA or DNA or modified RNA or DNA. "Polynucleotides" include, without limitation single-and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. In addition, "Polynucleotide" refers to triple-stranded regions comprising RNA or DNA or both RNA and DNA. The term Polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "Polynucleotide" embraces chemically, enzymatically or metabolically modified forms of polynucleotides as typically found in nature, as well as the chemical forms of DNA and RNA characteristic of viruses and cells, "Polynucleotide" also embraces relatively short polynucleotides, often referred to as oligonucleotides.

The term "polypeptide" refers to refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids.

The term "protein" refers to a sequence of more than 100 amino acids and/or to a multimeric entity. The proteins of the invention are not limited to a specific length of the product. The term "polypeptide" or "protein" does not refer to or exclude post-expression modifications of the protein, for example, glycosylation, acetylation, phosphorylation and the like, as well as other modifications known in the art, both naturally occurring and non-naturally occurring. Such modifications are well described in basic texts and in more detailed monographs, as well as in a voluminous research literature. Modifications can occur anywhere in a polypeptide or protein, including the peptide backbone, the amino acid side-chains and the amino or carboxyl termini. It will be appreciated that the same type of modification may be present in the same or varying degrees at several sites in a given polypeptide or protein. Also, a given polypeptide or protein may contain many types of modifications. Polypeptides or proteins may be branched as a result of ubiquitination, and they may be cyclic, with or without branching. Cyclic, branched and branched cyclic polypeptides or proteins may result from posttranslational natural processes or may be made by synthetic methods. Modifications include acetylation, acylation, ADP-ribosylation, amidation, covalent attachment of flavin, covalent attachment of a hem moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-linkings, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino of amino acids to proteins such as arginylation, and ubiquitination. See, for instance, "Proteins-structure and molecular properties", 2nd Ed., T. E. Creighton, W. H. Freeman and Comany, New York, 1993 Wolt, F., "Posttranslational Protein Modifications: Perspectives and Prospects" Posttranslational covalent modification of proteins, B. C. Johnson, Ed., Academic Press, New York, 1983, pgs. 1-12; Seifter et al., "Analysis for protein modifications and non-protein cofactors", Meth Enzymol, 1990, 182:626-646; Rattan et al, "Protein Synthesis: Posttranslational Modifications and Aging", Ann NY Acad Sri, 1992, 663:48-62. A protein may be an entire protein, or a subsequence thereof. An "isolated protein" is one that has been identified and separated and/or recovered from a component of its natural environment.

In a preferred embodiment, the isolated protein will be purified:
  (1) to greater than 80, 85, 90, 95% by weight of protein as determined by the Lowry method, and most preferably more than 96, 97, 98, or 99% by weight,
  (2) to a degree sufficient to obtain at least 15 residues of N-terminal or internal amino acid sequence by use of a spinning cup sequenator, or
  (3) to homogeneity by SDS-PAGE under reducing or non-reducing conditions using Coomassie blue or, preferably, silver staining.

Isolated protein includes the protein in situ within recombinant cells since at least one component of the protein's natural environment will not be present. Ordinarily, however, isolated protein will be prepared by at least one purification step.

The term "function-conservative fragment" refers to peptides derived from a peptide of the invention in which a given amino acid residue has been changed without altering the overall conformation and function of the peptide, including, but not limited to, replacement of an amino acid with one having similar properties (such as, for example, polarity, hydrogen bonding potential, acidic, basic hydrophobic, aromatic, and the like). Amino acids other than those indicated as conserved may differ in a protein so that the percent of protein or amino acid sequence similarity between any two proteins of similar function may vary and may be, for example, from 70% to 99% as determined according to an alignment method such as by the Cluster Method, wherein similarity is based on the MEG ALIGN algorithm. A "function-conservative variant" also includes a polypeptide which has at least 20% amino acid identity as determined by BLAST or FASTA algorithms, preferably 40% more preferably 60%, preferably at least 75%, most preferably at least 85%, and even more preferably at least 90%, and which has the same or substantially similar properties or functions as the native or parent protein to which it is compared.

The term "derivative" refers to a variation of a polypeptide of the invention or of a function-conservative variant thereof that are otherwise modified, i.e. by covalent attachment of any type of molecule to the polypeptide, by addition of chemical compound in any of the amino-acids of the sequence, in order to modify in vitro or in vivo conformation, activity, specificity, efficacy or stability of the polypeptide.

The term "agonist" refers to a natural or synthetic compound which binds to the protein and stimulates the biological activation of the protein, and thereby the action of the said protein. Consequently, "a CD47 agonist" includes any chemical entity that, upon administration to a subject, result in stimulation of a biological activity associated with CD47 in the patient, including any of the downstream biological effects otherwise resulting from the binding to CD47 of its natural ligand. Such CD47 agonists include any agent that can stimulate CD47 expression or any of the downstream biological effects of CD47.

The term "immunoglobulin" includes a polypeptide having a combination of two heavy and two light chains whether or not it possesses any relevant specific immunoreactivity. The term "antibodies" refers to combinations of two heavy and two light chains which have significant known specific immunoreactive activity to an antigen of interest (e.g. CD47, TSP1, HTRA1 or Fas). Antibodies and immunoglobulins comprise light and heavy chains, with or without an inter-chain covalent linkage between them. Basic immunoglobulin structures in vertebrate systems are relatively well understood. The generic term "immunoglobulin" comprises five distinct classes of antibody that can be distinguished biochemically. All five classes of antibodies are within the scope of the present invention, the following discussion will generally be directed to the IgG class of immunoglobulin molecules. With regard to IgG, immunoglobulins comprise two identical light polypeptide chains of molecular weight approximately 23,000 Daltons, and two identical heavy chains of molecular weight 53,000-70,000 Daltons. The four chains are joined by, disulfide bonds in a "Y" configuration wherein the light chains bracket the heavy chains starting at the mouth of the "Y" and continuing through the variable region. The light chains of an antibody are classified as either kappa or lambda ([κ], [λ]). Each heavy chain class may be bonded with either a kappa or lambda light chain. In general, the light and heavy chains are covalently bonded to each other, and the "tail" regions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon (γ, μ, α, δ, ε) with some subclasses among them (e.g., γ1-γ4). It is the nature of this chain that determines the "class" of the antibody as IgG, IgM, IgA, IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant invention. As indicated above, the variable region of an antibody allows the antibody to selectively recognize and specifically bind epitopes on antigens. That is, the VL domain and VH domain of an antibody combine to form the variable region that defines a three-dimensional antigen binding site. This quaternary antibody structure forms the antigen binding site present at the end of each arm of the Y. More specifically, the antigen binding site is defined by three complementarity determining regions (CDRs) on each of the VH and VL chains.

The term "monoclonal antibody" refers to an antibody obtained from a population of substantially homogeneous antibodies, i.e., the individual antibodies comprised in the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The term "polyclonal antibody" refers to a collection of immunoglobulin molecules that react against a specific antigen, each identifying a different epitope. Thus, contrary to monoclonal antibodies, polyclonal antibodies are not derived from a single cell line.

The term "antibody fragment" refers to a part or region of an antibody or antibody chain comprising fewer amino acid residues than an intact or complete antibody or antibody chain. The term "antigen-binding fragment" refers to a polypeptide fragment of an immunoglobulin or antibody that binds antigen or competes with intact antibody (i.e., with the intact antibody from which they were derived) for antigen binding (i.e., specific binding to CD47). As used herein, the term "antibody fragment" of an antibody molecule includes antigen-binding fragments of antibodies, for example, an antibody light chain variable domain (VL), an antibody heavy chain variable domain (VH), a single chain antibody (scFv), a F(ab')2 fragment, a Fab fragment, an Fd fragment, an Fv fragment, a single domain antibody fragment (Dab), a one-armed (monovalent) antibody, diabodies, triabodies, CDR1 CDR2, CDR3, combinations of CDR's, variable regions, tetrabodies, bifunctional hybrid antibodies, framework regions, constant regions, or any antigen-binding molecule formed by combination, assembly or conjugation of such antigen binding fragments. Fragments can be obtained, e.g., via chemical or enzymatic treatment of an intact or complete antibody or antibody chain or by recombinant means.

The term "derived from", before a designated protein (e.g. a TSP1 antibody or antigen-binding fragment thereof), refers to the origin of the polypeptide, in an embodiment, the polypeptide or amino acid sequence which is derived from a particular starting polypeptide is a CDR sequence or sequence related thereto. In an embodiment, the amino acid sequence which is derived from a particular starting polypeptide is not contiguous. For example, in an embodiment, one, two, three, four, five, or six CDRs are derived from a starting antibody. In an embodiment, the polypeptide or amino acid sequence which is derived from a particular starting polypeptide or amino acid sequence has an amino acid sequence that is essentially identical to that of the starting sequence, or a region thereof wherein the region consists of at least of at least 3-5 amino acids, 5-10 amino acids, at least 10-20 amino acids, at least 20-30 amino acids, or at least 30-50 amino acids, or which is otherwise identifiable to one of ordinary skill in the art as having its origin in the starting sequence.

The term "diabodies" refers to small antibody fragments prepared by constructing sFv fragments (see SFv paragraph) with short tinkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO93/11161; and Holliger et al., Proc. Natl. Acad. Sci 90:6444-6448 (1993).

The term "peptibodies": They consist of biologically active peptides grafted onto an Fc domain. This approach retains certain desirable features of antibodies, notably an increased apparent affinity through the avidity conferred by the dimerization of two Fcs. The term "epitope" refers to a specific arrangement of amino acids located on a peptide or protein or proteins to which an agent (e.g. an antibody or a small molecule) binds. Epitopes often consist of a chemically active surface grouping of molecules such as amino acids or sugar side chains, and have specific three dimensional structural characteristics as well as specific charge characteristics. Epitopes can be linear or conformational, i.e., involving two or more sequences of amino acids in various regions of the antigen that may not necessarily be contiguous.

The term "Fv" is the minimum antibody fragment that contains a complete antigen-recognition and -binding site. This fragment consists of a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability recognize and bind antigen, although at a lower affinity than the entire binding site.

The term "immunospecific", "specific for" or to "specifically bind": as used herein, an antibody is said to be "immunospecific", "specific for" or to "specifically bind" an antigen if it reacts at a detectable level with the antigen, preferably with an affinity constant, Ka, of greater than or equal to about $10^4 M^{-1}$, or greater than or equal to about $10^5$ $M^{-1}$, greater than or equal to about $10^6 M^{-1}$, greater than or equal to about $10^7 M^{-1}$, or greater than or equal to $10^8 M^{-1}$, or greater than or equal to $10^9 M^{-1}$, or greater than or equal to $10^{10} M^{-1}$. Affinity of an antibody for its cognate antigen is also commonly expressed as a dissociation constant Kd, and in certain embodiments, an antibody specifically binds to antigen if it binds with a Kd of less than or equal to $10^{-4}$ M, less than or equal to about $10^{-5}$ M, less than or equal to about $10^{-6}$ M, less than or equal to $10^{-7}$ M, or less than or equal to $10^{-8}$ M, or less than or equal to $5.10^{-9}$ M, or less than or equal to $10^{-9}$ M, or less than or equal to $5.10^{-10}$ M, or less than or equal to $10^{-10}$ M. Affinities of antibodies can be readily determined using conventional techniques, for example, those described by Scatchard G et al., (Ann NY Acad Sci. 1949, 51:660-672). Binding properties of an antibody to antigens, cells or tissues thereof may generally be determined and assessed using immunodetection methods including, for example, immunofluorescence-based assays, such as immuno-histochemistry (IHC) and/or fluorescence-activated cell sorting (FACS).

The term "mammal" refers to any mammal, including humans, domestic and farm animals, and zoo, sports, or pet animals, such as dogs, cats, cattle, horses, sheep, pigs, goats, rabbits, etc. Preferably, the mammal is human.

The term "synthetic" with respect to polypeptides includes polypeptides which comprise an amino acid sequence that is not naturally occurring. For example, non-naturally occurring polypeptides are modified forms of naturally occurring polypeptides (e.g., comprising a mutation such as an addition, substitution or deletion) or polypeptides which comprise a first amino acid sequence (which may or may not be naturally occurring) that is linked in a linear sequence of amino acids to a second amino acid sequence (which may or may not be naturally occurring) to which it is not naturally linked in nature.

The term "small molecule" means a low molecular weight molecule that include lipids, monosaccharides, second messengers, other natural products and metabolites. Small molecules are distinct from macromolecules such as proteins.

The term "binding site" comprises a region of a polypeptide which is responsible for selectively binding to a target antigen of interest (e.g. CD47, TSP1, HTRA1 or Fas). Binding domains or binding regions comprise at least one binding site. Exemplary binding domains include an antibody variable domain. The antibody molecules of the invention may comprise a single antigen binding site or multiple (e.g., two, three or four) antigen binding sites.

The term "siRNA" or "small interference RNA" refers to a double stranded structure containing from about 15 to about 50 base pairs, for example from about 21 to about 25 base pairs, and having a nucleotide sequence identical or nearly identical to an expressed target gene or RNA within the cell. The siRNA comprise a sense RNA strand and a complementary antisense RNA strand annealed together by standard Watson-Crick base-pairing interactions. The sense strand comprises a nucleic acid sequence which is substantially identical to a nucleic acid sequence contained within the target miRNA molecule. "Substantially identical" to a target sequence contained within the target mRNA refers to a nucleic acid sequence that differs from the target sequence by about 3% or less. The sense and antisense strands of the siRNA can comprise two complementary, single-stranded RNA molecules, or can comprise a single molecule in which two complementary portions are base-paired and are covalently linked by a single-stranded "hairpin" area. siRNA can be produced chemically or biologically, or can be expressed from a recombinant plasmid or viral vector through methods well-known to the one of skill in the art.

The term "antisense oligonucleotides" (or "ASOs") refers to small deoxy-oligonucleotides with a sequence complementary to the mRNA of the target gene. These oligonucleotides bind to the target mRNA through complementary base-pairing and attract the binding of RNase H, an enzyme that degrades double strand RNA, thus destroying the target mRNA.

The term "treatment" or "treating" refers to both therapeutic treatment and prophylactic or preventative measures; wherein the object is to prevent or slow down (lessen) inflammation. Those in need of treatment include those already with inflammation as well as those prone to have inflammation or those in whom inflammation is to be prevented. A subject or mammal is successfully "treated" for inflammation if, after receiving a therapeutic amount of an agent according to the present invention, the patient shows observable and/or measurable reduction in or absence of one or more of the following: relief to some extent, one or more of the symptoms associated inflammation; reduced morbidity and mortality, and improvement in quality of life issues. The above parameters for assessing successful treatment and improvement in the disease are readily measurable by routine procedures familiar to a physician.

The term "subject" refers to a mammal, preferably a human. In one embodiment, the subject is a man. In another embodiment, the subject is a woman. In one embodiment, a subject may be a "patient", i.e. a warm-blooded animal, more preferably a human, who/which is awaiting the receipt of, or is receiving medical care or was/is/will be the object of a medical procedure, or is monitored for the development of inflammation. In one embodiment, the subject is an adult (for example a subject above the age of 18). Another embodiment, the subject is a child (for example, a subject below the age of 18). In one embodiment the compound of the invention is administered to a human patient in need thereof.

The term "therapeutically effective amount" means the level or amount of agent that is aimed at, without causing significant negative or adverse side effects to the target, (1) delaying or preventing the onset of inflammation; (2) slowing down or stopping the progression, aggravation, or deterioration of one or more symptoms of inflammation; (3) bringing about ameliorations of the symptoms of inflammation; (4) reducing the severity or incidence of inflammation; or (5) curing inflammation. A therapeutically effective amount may be administered prior to the onset of inflammation, for a prophylactic or preventive action. Alternatively or additionally, the therapeutically effective amount may be administered after initiation of inflammation, for a therapeutic action or maintenance of a therapeutic action.

The term "pharmaceutically acceptable excipient" refers to an excipient that does not produce an adverse, allergic or other untoward reaction when administered to an animal, preferably a human. It includes any and all solvents, dispersion media, coatings, antibacterial and antifungal agents, isotonic and absorption delaying agents and the like. A pharmaceutically acceptable carrier or excipient refers to a non-toxic solid, semi-solid or liquid filler, diluent, encapsulating material or formulation auxiliary of any type. Far human administration, preparations should meet sterility, pyrogenicity, general safety and purity standards as required by FDA Office of Biologics standards.

The term "about" preceding a value means plus or less 10% of said value.

DETAILED DESCRIPTION

The present invention relates to a multimeric peptide or polypeptide comprising at least two peptide monomers linked to one another, wherein said at least two peptide monomers activates CD47.

In one embodiment, the multimeric peptide or polypeptide of the invention comprises the amino acid of 4N1K peptide (sequence KRFYVVMWKK, SEQ ID NO: 1), PKHB1 peptide (sequence (D)K-R-F-Y-V-V-M-W-K-(D)K, formula I) and/or PKT16 peptide (sequence (D)K-(NMeR)-F-Y-V-V-Nle-W-K-(D)K, formula II), or function-conservative fragments thereof.

conservative fragments thereof. In one embodiment, the multimeric peptide or polypeptide of the invention comprises at least one PKHB1 peptide and at least one PKT16 peptide, or function-conservative fragments thereof.

Formula I

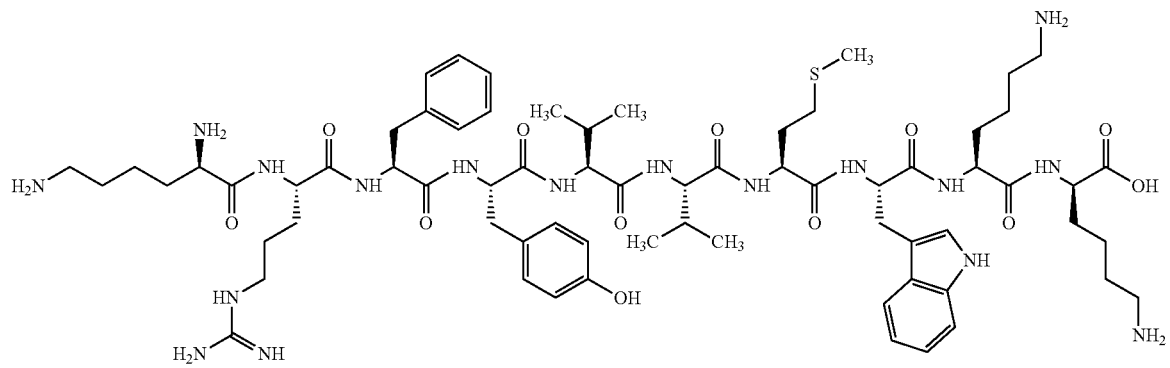

Formula II

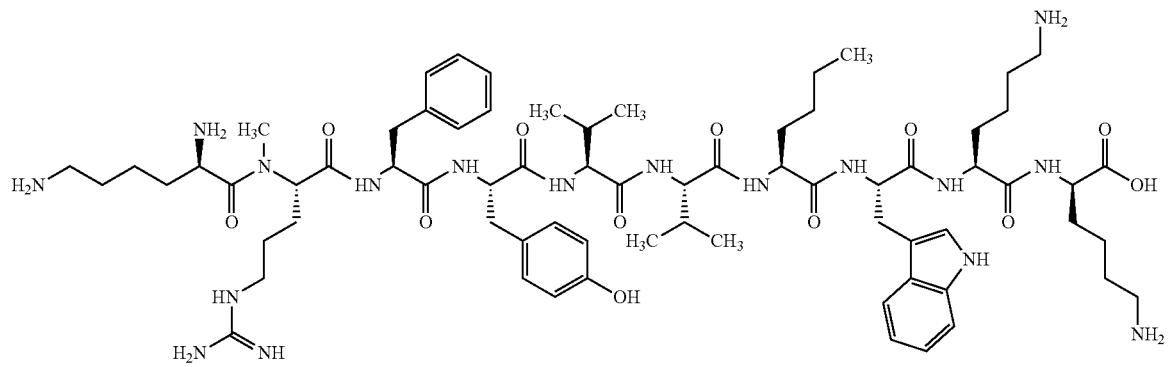

In one embodiment, the multimeric peptide or polypeptide comprises at least 5 consecutive amino acids selected from the amino acid sequence SEQ ID NO: 1 and a function-conservative fragment. In another embodiment, the agent of embodiment, the activating polypeptide or protein of the invention comprises at least 6, 7, 8, 9 or 10 consecutive amino acids selected from the amino acid sequence SEQ ID NO: 1 and a function-conservative fragment.

In one embodiment, the at least two peptide monomers are identical or different. As an illustration, in one embodiment, the multimeric peptide or polypeptide may comprise two 4N1K peptides. Still as an example, in another embodiment, the multimeric peptide or polypeptide may comprise one 4N1K peptide and a PKT16 peptide.

In one embodiment, the multimeric peptide or polypeptide of the invention comprises at least two 4N1K peptides or function-conservative fragments thereof. In one embodiment, the multimeric peptide or polypeptide of the invention comprises at least two peptides or function-conservative fragments thereof. In one embodiment, the multimeric peptide or polypeptide of the invention comprises at least two PKT16 peptides or function-conservative fragments thereof.

In one embodiment, the multimeric peptide or polypeptide of the invention comprises at least one 4N1K peptide and at least one PKHB1 peptide, or function-conservative fragments thereof. In one embodiment, the multimeric peptide or polypeptide of the invention comprises at least one 4N1K peptide and at least one PKT16 peptide, or function- In one embodiment, the multimeric peptide or polypeptide of the invention comprises any number of repeating units. In one embodiment, the multimeric peptide or polypeptide of the invention comprises 2 to 10, 2 to 20, or 2 to 30 repeating subunits. In one embodiment, the multimeric peptide or polypeptide of the invention comprises 2, 3, 4, 5, 6, 7, 8, 9, 10, 11, or 12 repeating subunits. Accordingly, in one embodiment, the multimeric peptide or polypeptide of the invention may be a dimer, a trimer, a, tetramer, a pentamer, a hexamer, a heptamer, an octamer, a nonamer, a decamer, an undecamer or a dodecamer.

In a particular embodiment, the multimeric peptide or polypeptide of the invention comprises 2, 3, 4, 5, 6, 7, 8, 9, 10, 11, or 12 4N1K peptides. Accordingly, in a particular embodiment, the multimeric peptide or polypeptide of the invention is a dimer, a trimer, a tetramer, a pentamer, a hexamer, a heptamer, an octamer, a nonamer, a decamer, an undecamer or a dodecamer of 4N1K peptides. In a particular embodiment, the multimeric peptide or polypeptide of the invention is a dimer of 4N1K.

In one embodiment, linking of the peptide monomers of the invention may be effected using any method known in the art provided that the linking does not substantially interfere with the bioactivity of the multimeric peptide, polypeptide or protein, i.e. to activate CD47.

In one embodiment, the peptide monomers of the present invention may be linked through a linking moiety.

Examples of linking moieties include, but are not limited to, a simple covalent bond, a flexible peptide linker, an alkyl linker, a disulfide bridge or a polymer such as polyethylene glycol (PEG). Peptide linkers may be entirely artificial (e.g., comprising 2 to 20 amino acid residues independently selected from the group consisting of glycine, serine, asparagine, threonine and alanine) or adopted from naturally occurring proteins. Disulfide bridge formation can be achieved, e.g., by addition of cysteine residues, as further described herein below. Linking through polyethylene glycols (PEG) can be achieved by reaction of monomers having free cysteines with multifunctional PEGs, such as linear bis-maleimide PEGs. Alternatively, linking can be performed though the glycans on the monomer after their oxidation to aldehyde form and using multifunctional PEGs containing aldehyde-reactive groups. Selection of the position of the link between the two monomers should take into account that the link should not substantially interfere with the ability of the multimeric peptide or polypeptide to activate CD47.

In one embodiment, the linking moiety is a peptide linker.

In one embodiment, the peptide linker of the invention has a length of 3 to 30 amino acids, preferably from 4 to 20 amino acids, more preferably from 5 to 15 amino acids. In one embodiment, the peptide linker of the invention comprises at least 4, 5, 6, 7, 8, 9, 10, 11, 12 or 15 amino acids. In one embodiment, the peptide linker of the invention comprises at most 20, 19, 18, 17, 16, 15, 14, 13 or 12 amino acids.

In one embodiment, the peptide linker of the invention comprises 3, 4, 5, 6, 7, 8 or 9 amino acids. In another embodiment, the peptide linker of the invention comprises 10, 11, 12, 13, 14, 15, 16, 17, 18, 19, 20 or more amino acids.

Examples of peptide linker include, but are not limited to, Gly-rich linkers such as poly-Gly linkers, Ser-rich linkers, linkers comprising stretches of Gly and Ser residues (also called "GS linkers"), Pro-rich linkers, helical linkers, and the like.

In one embodiment, the amino acids of the peptide linker are selected from the 20 naturally-occurring amino acids. In a preferred embodiment, the 1 to 20 amino acids are selected from Gly, Ala, Pro, Asn, Gln, Cys, Lys. In a more preferred embodiment, the linker is made up of a majority of amino acids that are sterically un-hindered, such as Gly, Gly-Gly [(Gly)$_2$], Gly-Gly-Gly [(Gly)$_3$] . . . (Gly)$_{20}$, Ala, Gly-Ala, Ala-Gly, Ala-Ala, etc. Other specific examples of linkers are: (Gly)$_3$Lys(Gly)$_4$ (SEQ ID NO: 2); (Gly)$_3$AsnGlySer (Gly)$_2$ (SEQ ID NO: 3) (this structure provides a site for glycosylation, when it is produced recombinantly in a mammalian cell system that is capable of glycosylating such sites); (Gly)$_3$Cys(Gly)$_4$ (SEQ ID NO: 4); and GlyProAsnGly (SEQ ID NO: 5).

In a preferred embodiment, the peptide linker is Gly-Gly-Gly-Gly-Gly-Gly-Gly-Gly [(Gly)$_8$, SEQ ID NO: 6]. In another preferred embodiment, the peptide linker is a combination of Gly and Ala. In another preferred embodiment, the peptide linker is a combination of Gly and Lys.

In one embodiment, the multimeric peptide or polypeptide of the invention comprises two 4N1K peptides linked through a peptide linker, preferably a Gly-rich linker. In another embodiment, the multimeric peptide or polypeptide of the invention comprises two PKHB1 peptides linked through a peptide linker, preferably a Gly-rich linker. In one embodiment, the multimeric peptide or polypeptide of the invention comprises two PKT16 peptides linked through a peptide linker, preferably a Gly-rich linker.

In a particular embodiment, the multimeric peptide or polypeptide of the invention comprises or consists of the amino acid sequence SEQ ID NO: 7.

The present invention also relates to a polynucleotide or nucleic acid sequence encoding the multimeric peptide or polypeptide as described hereinabove.

In one embodiment, the polynucleotide or nucleic acid is DNA. In another embodiment, the polynucleotide of the invention is RNA, for example, in the form of messenger RNA (mRNA). RNA of the present invention may be single stranded or double stranded.

Another object of the present invention is a vector comprising one or more polynucleotides encoding a multimeric peptide or polypeptide of the invention. In a preferred embodiment, the vector of the invention is an expression vector.

A further object of the invention is a composition comprising a multimeric peptide or polypeptide or a polynucleotide of the invention as described hereinabove.

Another object of the present invention is a modified TSP1 protein resistant to the protease HTRA1 (HTRA1-resistant modified TSP1) or a fragment thereof, wherein said modified TSP1 protein activates CD47.

The Applicant shows that HTRA1 cleaves TSP1 at (i) a site known for its binding capacity to the integrin α3β1, (ii) at two sites between the "type 2" domains, and (iii) at two sites between the two valine-valine-methionine (VVM) sequences that can each interact with a CD47 receptor and are responsible for its highly efficient CD47 activation (see Example 4). However, the protein TSP2, which shares the same overall structure and interacts with a number of the same cell-surface receptors including CD47, is resistant to the protease HTRA1.

In one embodiment, a fragment of a modified TSP1 protein resistant to the protease HTRA1 comprises from 50 to 1100 amino acids, from 100 to 1000, 900, 800, 700, 600, 500, or 400 amino acids of the modified TSP1 protein. In another embodiment, the fragment of the invention comprises from 150 to 1100, 1000, 900, 800, 700, 600, 500 or 400 amino acids of the modified TSP1 protein. In another embodiment, the fragment of the invention comprises from 200 to 1100, 1000, 900, 800, 700, 600, 500 or 400 amino acids of the modified TSP1 protein. In another embodiment, the fragment of the invention comprises from 300 to 1100, 1000, 900, 800, 700, 600, 500 or 400 amino acids of the modified TSP1 protein. In a particular embodiment, the fragment of the invention comprises 369 amino acids of the modified TSP1 protein.

In one embodiment, the fragment of the invention comprises or consists of the C-terminal portion of the modified TSP1 protein. In a preferred embodiment, the fragment of the invention comprises or consists of the last 369 amino acids of the modified TSP1 protein.

In one embodiment, the modified TSP1 protein or fragment thereof have retained the capacity to bind CD47, whilst being resistant to the protease HTRA1.

In one embodiment, the HTRA1-resistant modified TSP1 of the invention is a modified TSP1 protein wherein at least one amino acid of at least one of the HTRA1-cleavage sequences is deleted, substituted or added.

As used herein, the term "HTRA1-cleavage sequences" means the sequences in the amino acid sequence of TSP1 cleaved by the protease HTRA1. In one embodiment, the at least one HTRA1-cleavage sequence of TSP1 is QVTQ in position 241-244 of SEQ ID NO: 8. In one embodiment, the at least one HTRA1-cleavage sequence of TSP1 is GQVR in position 287-290 of SEQ ID NO: 8.

In one embodiment, the HTRA1-resistant modified TSP1 of the invention is a modified TSP1 protein wherein at least one amino acid of at least one of the HTRA1-cleavage sequences is deleted.

In one embodiment, the HTRA1-resistant modified TSP1 of the invention is a modified TSP1 protein wherein the residues VT in position 242-243 of SEQ ID NO: 8 are deleted. In one embodiment, the HTRA1-resistant modified TSP1 of the invention is a modified TSP1 protein wherein the residues QV in position 288-289 of SEQ ID NO: 8 are deleted. In one embodiment, the HTRA1-resistant modified TSP1 of the invention is a modified TSP1 protein wherein the residues VT in position 242-243 and the residues QV in position 288-289 of SEQ ID NO: 8 are deleted.

In one embodiment, the amino acid sequence of the HTRA1-resistant modified TSP1 or fragment thereof of the invention comprises a sequence at least 75% identical to SEQ ID NO: 9. In one embodiment, the amino acid sequence of the HTRA1-resistant modified TSP1 or fragment thereof of the invention comprises a sequence at least 80%, 85%, 90%, 95%, 96%, 97%, 98%, 99% or more identical to SEQ ID NO: 9. In one embodiment, the HTRA1-resistant modified TSP1 or fragment thereof of the invention has an amino acid sequence comprising or consisting of SEQ ID NO: 9. In one embodiment, the HTRA1-resistant modified TSP1 of the invention has a C-terminal portion having the amino acid sequence of SEQ ID NO: 9. In one embodiment, the HTRA1-resistant modified TSP1 fragment of the invention has an amino acid sequence consisting of SEQ ID NO: 9.

In one embodiment, the HTRA1-resistant modified TSP1 of the invention is a modified TSP1 protein wherein at least one amino acid of at least one of the HTRA1-cleavage sequences is substituted.

In one embodiment, the HTRA1-resistant modified TSP1 of the invention is a modified TSP1 protein wherein the residue V in position 242 of SEQ ID NO: 8 is substituted. In one embodiment, the HTRA1-resistant modified TSP1 of the invention is a modified TSP1 protein wherein the residue V in position 289 of SEQ ID NO: 8 is substituted. In one embodiment, the HTRA1-resistant modified TSP1 of the invention is a modified TSP1 protein wherein the residues V242 and V289 of SEQ ID NO: 8 are substituted.

In one embodiment, the substitution is an amino acid substitution selected from the group comprising or consisting of A, C, D, F, G, H, I, L, M, N, P, Q, R, S, V, W, and Y. In a particular embodiment, the substitution the amino acid N. In one embodiment, the HTRA1-resistant modified TSP1 or fragment thereof is a modified TSP1 protein comprising the substitution V242N (in position according to SEQ ID NO: 8). In another embodiment, the HTRA1-resistant modified TSP1 or fragment thereof is a modified TSP1 protein comprising the substitution V289N (in position according to SEQ ID NO: 8). In another embodiment, the HTRA1-resistant modified TSP1 or fragment thereof is a modified TSP1 protein comprising the substitutions V242N and V289N (in position according to SEQ ID NO: 8).

In one embodiment, the amino acid sequence of the HTRA1-resistant modified TSP1 or fragment thereof comprises a sequence at least 75% identical to SEQ ID NO: 11. In one embodiment, the amino acid sequence of the HTRA1-resistant modified TSP1 or fragment thereof comprises a sequence at least 80%, 85%, 90%, 95%, 96%, 97%, 98%, 99% or more identical to SEQ ID NO: 11. In one embodiment, the HTRA1-resistant modified TSP1 or fragment thereof has an amino acid sequence comprising or consisting of SEQ ID NO: 11. In one embodiment, the HTRA1-resistant modified TSP1 of the invention has a C-terminal portion having the amino acid sequence of SEQ ID NO: 11. In one embodiment, the HTRA1-resistant modified TSP1 fragment of the invention has an amino acid sequence consisting of SEQ ID NO: 11.

In one embodiment, the amino acid sequence of the HTRA1-resistant modified TSP1 or fragment thereof further comprises at least one cysteine substitution. In one embodiment, the at least one cysteine substituted is selected from the group comprising C3, C15, C34, C35, C55, C73, C93, C109, C129, C145, C191 and C366 (position according to SEQ ID NO: 8). In one embodiment, the at least one cysteine substituted is C34 (position according to SEQ ID NO: 8). In another embodiment, the at least one cysteine substituted is C191 (position according to SEQ ID NO: 8). In one embodiment, the amino acid sequence of the HTRA1-resistant modified TSP1 or fragment thereof further comprises two cysteine substitutions. In one embodiment, the two cysteines substituted are C34 and C191 (position according to SEQ ID NO: 8).

In one embodiment, the amino acid sequence of the HTRA1-resistant modified TSP1 or fragment thereof of the invention comprises a sequence at least 75% identical to SEQ ID NO: 10. In one embodiment, the amino acid sequence of the HTRA1-resistant modified TSP1 or fragment thereof of the invention comprises a sequence at least 80%, 85%, 90%, 95%, 96%, 97%, 98%, 99% or more identical to SEQ ID NO: 10. In one embodiment, the HTRA1-resistant modified TSP1 or fragment thereof of the invention has an amino acid sequence comprising or consisting of SEQ ID NO: 10. In one embodiment, the HTRA1-resistant modified TSP1 of the invention has a C-terminal portion having the amino acid sequence of SEQ ID NO: 10. In one embodiment, the HTRA1-resistant modified TSP1 fragment of the invention has an amino acid sequence consisting of SEQ ID NO: 10.

In one embodiment, the amino acid sequence of the HTRA1-resistant modified TSP1 or fragment thereof comprises a sequence at least 75% identical to SEQ ID NO: 12. In one embodiment, the amino acid sequence of the HTRA1-resistant modified TSP1 or fragment thereof comprises a sequence at least 80%, 85%, 90%, 95%, 96%, 97%, 98%, 99% or more identical to SEQ ID NO: 12. In one embodiment, the HTRA1-resistant modified TSP1 or fragment thereof has an amino acid sequence comprising or consisting of SEQ ID NO: 12. In one embodiment, the HTRA1-resistant modified TSP1 of the invention has a C-terminal portion having the amino acid sequence of SEQ ID NO: 12. In one embodiment, the HTRA1-resistant modified TSP1 fragment has an amino acid sequence consisting of SEQ ID NO: 12.

In one embodiment, the HTRA1-resistant modified TSP1 or fragment thereof is a modified TSP1 protein or fragment thereof wherein the HTRA1-cleavage sequences are replaced by the HTRA1-resistant sequences of TSP2.

In one embodiment, the amino acid sequence of the HTRA1-resistant modified TSP1 comprises a sequence at least 75% identical to SEQ ID NO: 13. In one embodiment, the amino acid sequence of the HTRA1-resistant modified TSP1 comprises a sequence at least 80%, 85%, 90%, 95%, 96%, 97%, 98%, 99% or more identical to SEQ ID NO: 13. In one embodiment, the HTRA1-resistant modified TSP1 thereof has an amino acid sequence comprising or consisting of SEQ ID NO: 13.

In one embodiment the HTRA1-resistant derived TSP2 of the invention is a chimeric TSP2/TSP1 recombinant protein comprising (i) the amino acid sequence of TSP2 and (ii) the amino acid sequence of the TSP1 tail, wherein the TSP1 tail comprises the second VVM sequence of TSP1. In one embodiment, the amino acid sequence of the TSP1 tail comprising its second VVM sequence is located at the N-terminus of the chimeric TSP2/TSP1 recombinant protein.

In one embodiment, the HTRA1-resistant derived TSP2 of the invention comprises a sequence at least 75% identical to SEQ ID NO: 14. In one embodiment, the HTRA1-resistant derived TSP2 of the invention comprises a sequence at least 80%, 85%, 90%, 95%, 96%, 97%, 98%, 99% or more identical to SEQ ID NO: 14. In one embodiment, the HTRA1-resistant derived TSP2 of the invention has an amino acid sequence comprising or consisting of SEQ ID NO: 14.

The present invention also relates to a polynucleotide or nucleic acid sequence encoding a modified TSP1 protein resistant to the protease HTRA1 or a fragment thereof as described hereinabove.

In one embodiment, the polynucleotide or nucleic acid is DNA. In another embodiment, the polynucleotide of the invention is RNA, for example, in the form of messenger RNA (mRNA). RNA of the present invention may be single stranded or double stranded.

Another object of the present invention is a vector comprising one or more polynucleotides encoding a modified TSP1 protein resistant to the protease HTRA1 or a fragment thereof according to the invention. In a preferred embodiment, the vector of the invention is an expression vector.

A further object of the invention is a composition comprising a modified TSP1 protein resistant to the protease HTRA1 or a fragment thereof, or a polynucleotide according to the invention as described hereinabove.

In one embodiment, the multimeric peptide or polypeptide of the invention, or the modified TSP1 protein resistant to the protease HTRA1 or a fragment thereof according to the invention, have modifications rendering the peptide, polypeptide or protein more stable while in a body or more capable of penetrating into cells.

Such modifications include, but are not limited to, N terminus modification, C terminus modification, peptide bond modification, including, but not limited to, CH2-NH, CH2-S, CH2-S=0, 0=C—NH, CH2-0, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992).

In one embodiment, peptide bonds (—CO—NH—) within the peptide may be substituted, for example, by N-methylated bonds (—N(CH3)-CO—), ester bonds (—C(R)H—C-0-0-C(R)—N—), ketomethylen bonds (—CO—CH2-), a-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

In one embodiment, these modifications can occur at any of the bonds along the peptide chain and even at several (2-3) at the same time.

In one embodiment, natural aromatic amino acids, Trp, Tyr and Phe, may be substituted for synthetic non-natural acid such as Phenylglycine, TIC, naphthylelanine (Nol), ring-methylated derivatives of Phe, halogenated derivatives of Phe or o-methyl-Tyr.

In one embodiment, peptides, polypeptides or proteins of the invention may further be linear or cyclic. By "cyclic" is meant that at least two separated, i.e., non-contiguous, portions of the molecule are linked to each other. For example, the amino and carboxy terminus of the ends of the molecule could be covalently linked to form a cyclic molecule. Alternatively, the molecule could contain two or more Cys residues (e.g., in the linker), which could cyclize via disulfide bond formation. It is further contemplated that more than one tandem peptide dimer can link to form a dimer of dimers. Thus, for example, a tandem dimer containing a Cys residue can form an intermolecular disulfide bond with a Cys of another such dimer.

In one embodiment peptides, polypeptides or proteins of the invention may also be covalently or noncovalently associated with a carrier molecule, such as a linear polymer (e.g., polyethylene glycol, polylysine, dextran, etc.), a branched-chain polymer; a lipid; a cholesterol group (such as a steroid) or a carbohydrate or oligosaccharide.

Other possible carriers include one or more water soluble polymer attachments such as polyoxyethylene glycol, or polypropylene glycol. Still other useful polymers known in the art include monomethoxy-polyethylene glycol, dextran, cellulose, or other carbohydrate based polymers, poly-(N-vinyl pyrrolidone)- polyethylene glycol, propylene glycol homopolymers, a polypropylene oxide/ethylene oxide co-polymer, polyoxyethylated polyols (e.g., glycerol) and polyvinyl alcohol, as well as mixtures of these polymers.

In a preferred embodiment, the carrier is polyethylene glycol (PEG). In one embodiment, the PEG group may be of any convenient molecular weight and may be straight chain or branched. In one embodiment, the average molecular weight of the PEG will preferably range from about 2 kDa to about 100 kDa, more preferably from about 5 kDa to about 50 kDa, most preferably from about 5 kDa to about 10 kDa.

In one embodiment, PEG groups are attached to the compounds of the invention via acylation reductive alkylation Michael addition, thiol alkylation or other chemoselective conjugation/ligation methods through a reactive group on the PEG moiety (e.g., an aldehyde, amino, ester, thiol, ct-haloacetyl, maleimido or hydrazino group) to a reactive group on the target compound (e.g., an aldehyde, amino, ester, thiol, a-haloacetyl, maleimido or hydrazino group).

In one embodiment, carbohydrate (oligosaccharide) groups are attached to sites that are known to be glycosylation sites in proteins. Generally, O-linked oligosaccharides are attached to serine (Ser) or threonine (Thr) residues while N-linked oligosaccharides are attached to asparagine (Asn) residues when they are part of the sequence Asn-X-Ser/Thr, where X can be any amino acid except proline. X is preferably one of the 19 naturally occurring amino acids not counting proline. The structures of N-linked and O-linked oligosaccharides and the sugar residues found in each type are different. One type of sugar that is commonly found on both is N-acetylneuraminic acid (referred to as sialic acid). Sialic acid is usually the terminal residue of both N-linked and O-linked oligosaccharides and, by virtue of its negative charge, may confer acidic properties to the glycosylated compound. Such site (s) may be incorporated in the linker of the compounds of this invention and are preferably glycosylated by a cell during recombinant production of the polypeptide compounds (e.g., in mammalian cells such as CHO, BHK, COS). However, such sites may further be glycosylated by synthetic or semi-synthetic procedures known in the art.

In one embodiment, peptides, polypeptides or proteins described above may further be fused to one or more Fc polypeptides, either directly or through linker groups.

In one embodiment, the Fc sequence of the above compounds may be selected from the human immunoglobulin IgG-1 heavy chain, see Ellison, J. W. et al., Nucleic Acids Res. 10: 4071-4079 (1982), or any other Fc sequence known in the art (e.g. other IgG classes including but not limited to IgG-2, IgG-3 and IgG-4, or other immunoglobulins).

It is well known that Fc regions of antibodies are made up of monomeric polypeptide segments that may be linked into dimeric or multimeric forms by disulfide bonds or by non-covalent association. The number of intermolecular disulfide bonds between monomeric subunits of native Fc molecules ranges from 1 to 4 depending on the class (e.g., IgG, IgA, IgE) or subclass (e.g., IgG1. IgG2, IgG3, IgGA2) of antibody involved. As used herein, the term "Fc" is generic to the monomeric, dimeric, and multimeric forms of Fc molecules. It should be noted that Fc monomers will spontaneously dimerize when the appropriate Cys residues are present unless particular conditions are present that prevent dimerization through disulfide bond formation.

In one embodiment, the Fc polypeptides may be any variants having longer in vivo half lives than control Fc polypeptides. Examples of variants of Fc polypeptides include, but are not limited to, Fc polypeptides binding to FcRn with a higher affinity than control Fc polypeptides at a slightly acidic pH, Fc polypeptides binding to FcRn with the same or a lower affinity than control Fc polypeptides at physiologic pH, Fc polypeptides comprising an insertion of 3 to 20 amino acids within or adjacent to loop 5, 8, and/or 10, and the like.

In one embodiment, the protein of the invention comprises at least one multimeric peptide as described above, further be fused to one or more Fc groups. In a preferred embodiment, the protein of the invention comprises at least one multimeric peptide comprising two 4N1K peptides linked through a peptide linker, preferably a Gly-rich linker, further be fused to one or more Fc groups.

In a particular embodiment, the protein of the invention comprises two multimeric peptides comprising two 4N1K peptides linked through a peptide linker, each of them further be fused to a Fc polypeptide.

The Applicant here shows that $CD47^{-/-}$, but not $CD36^{-/-}$-mice develop age-, light- and laser-induced subretinal mononuclear phagocytes accumulation similar to $Tsp1^{-/-}$-mice (see Example 1). $Tsp1^{-/-}$- and $CD47^{-/-}$-microglial cells, adoptively transferred to the subretinal space of wildtype recipients significantly resisted to elimination compared to wildtype microglial cells and recombinant TSP1 very significantly accelerated the elimination of wildtype microglial cells and reversed the phenotype of $Tsp1^{-/-}$-microglial cells but had no effect on $CD47^{-/-}$-microglial cells, confirming that the interaction of TSP1 and CD47 mediates microglial cells elimination (see Example 1). The Applicant also demonstrates that HTRA1 is robustly expressed in early monocyte macrophage differentiation and that the SNP rs11200638 significantly increases HTRA1 expression (see Example 2). The Applicant shows that HTRA1 proteolyzes TSP1 at 5 distinct sites, 2 of which are located between the two Valine-Valine-Methionine sites that are necessary for efficient CD47 activation (see Examples 3 and 4). Moreover, in vitro, recombinant HTRA1 significantly increased mononuclear phagocytes survival co-cultured with RPE cells and activation of CD47 by an activating peptide (see Example 5) and more efficiently so by an activating peptide that contains two CD47 binding sites (see Example 6), or co-activation of CD47 by TSP-1 and FAS by Mega FasL, reversed this effect (see Example 5). In vivo, the Applicant shows that intravitreal injections of recombinant TSP-1 or a CD47 activating peptide, after laser-induced subretinal inflammation in inflammation-prone Cx3cr1 deficient mice, efficiently accelerated the elimination of subretinal mononuclear monocytes (see Example 6). Furthermore, recombinant TSP-1 or a CD47 activating peptide efficiently accelerated the elimination of inflammatory macrophages in a model of sterile peritonitis (see Example 6). In summary, the inventors show that (i) CD47 activation and (ii) the combined activation of CD47 and FAS efficiently eliminates mononuclear phagocytes.

Therefore, the present invention relates to an agent for use in the treatment of inflammation, wherein the agent activates CD47. In one embodiment, the agent activating CD47 is used for treating (or for use in treating) inflammation.

Within the meaning of the invention, the term "activating" means that the agent is capable of activating the biological activity of the target protein, directly or indirectly. In a particular embodiment, an agent activating CD47 is an agent capable of activating CD47 biological activity, in activating CD47 either directly or indirectly.

In one embodiment, the agent of the invention directly activates CD47. Examples of agents directly activating CD47 include, but are not limited to, agonists of CD47, activating antibodies, activating peptides, activating polypeptides, activating proteins, peptibodies, and the like.

As used herein, the term "agonists of CD47" means proteins and peptides capable to bind the receptor CD47 and to activate it to produce its biological activity.

In on, embodiment, the agonist of CD47 is its natural ligand TSP-1, a TSP1 variant, a TSP1 fragment or a TSP1 peptidomimetic that have retained the capacity of TSP1 to bind CD47 and to trigger the downstream biological effects of CD47 activation, i.e. the elimination of mononuclear phagocytes in cells.

In one embodiment, the TSP1 variant, fragment or peptidomimetic is a modified TSP1 protein which is resistant to the protease HTRA1 (HTRA1-resistant modified TSP1) or a fragment thereof as defined hereinabove.

In another embodiment, the TSP1 variant, fragment or peptidomimetic is a derived TSP2 protein which have retained the capacity to bind CD47, whilst being resistant to the protease HTRA1 (HTRA1-resistant derived TSP2) as defined hereinabove.

In another embodiment, the agonist of CD47 is its natural ligand SIRPα, a SIRPα variant, a SIRPα fragment or a SIRPα peptidomimetic.

In one embodiment, the agonist of CD47 is an activating antibody. Examples of activating antibodies include, but are not limited to, antibody Ad22 (Pettersen et al., J. Immunol. 1999, 162(12):7031-40), antibody 1F7 (Manna et al., J Biol Chem. 2005, 280:29637-29644), and antibody MABL (Uno et al., Oncology Reports. 2007, 17(5):1189-1194).

In another embodiment, the agonist of CD47 is an activating peptide. Examples of activating peptides include, but are not limited to, 4N1K peptide (SEQ ID NO: 1); PKHB1 peptide (formula I); and PKT16 peptide (formula II).

In one embodiment, the activating peptide of the invention has a length of 5 to 15 amino acids, or 6 to 14 amino acids, or 7 to 13 amino acids, or 8 to 12 amino acids, or 9 to 11 amino acids. In another embodiment, the activating peptide of the invention has a length of 5 to 14 amino acids, or 5 to 13 amino acids, or 5 to 12 amino acids, or 5 to 11 amino acids, or 5 to 10 amino acids, in another embodiment, the activating peptide of the invention has a length of 6 to 15 amino acids, or 7 to 15 amino acids, or 8 to 15 amino acids, or 9 to 15 amino acids, or 10 to 15 amino acids.

In one embodiment, the activating peptide of the invention comprises the amino acid of SEQ ID NO: 1. In one embodiment, the activating peptide of the invention comprises at least 5 consecutive amino acids selected from the amino acid sequence SEQ ID NO: 1 and a function-conservative fragment. In a particular CD47 is selected from the group comprising TSP1 activators, HTRA1 inhibitors and Fas activators.

In another embodiment, the agent of embodiment, the activating peptide of the invention comprises at least 6, 7, 8, 9 or 10 consecutive amino acids selected from the amino acid sequence SEQ ID NO: 1 and a function-conservative fragment. In a preferred embodiment, the activating peptide of the invention consists of the amino acid of SEQ ID NO: 1.

In one embodiment, the activating peptide of the invention is selected from the group comprising 4N1K, PKHB1, PKT16, and function-conservative fragments thereof. In one embodiment, the activating peptide of the invention is PKHB1, PKT16, or function-conservative fragments thereof. In one embodiment, the activating peptide of the invention is PKHB1 or function-conservative fragments thereof. In another embodiment, the activating peptide of the invention is PKT16 or function-conservative fragments thereof.

In one embodiment, the agonist of CD47 is a multimeric peptide or polypeptide as defined hereinabove. In one embodiment, the agonist of CD47 is a multimeric peptide or polypeptide comprising at least one 4N1K peptide. In one embodiment, the multimeric peptide or polypeptide comprises 2, 3, 4, 5, 6, 7, 8, 9, 10, 11, or 12 repeating subunits, preferably of the 4N1K peptide. In a particular embodiment, the agonist of CD47 is a multimeric peptide comprising or consisting of the amino acid sequence SEQ ID NO: 7. In another embodiment, the agent of the invention indirectly activates CD47. In one embodiment, the agent of the invention that indirectly activates the invention is a HTRA1 inhibitor. Examples of HTRA1 inhibitors include, but are not limited to, antibodies directed against HTRA1, variants or fragments thereof, siRNAs and antisense oligonucleotides (ASOs) directed against the gene and/or the transcript of the HTRA1 gene.

In another embodiment, the agent of the invention is a Fas activator. Examples of Fas activators include, but are not limited to, proteins and peptides capable to bind Fas and to activate the formation of DISC, as well as FasL variants, fragments or peptidomimetics that have retained the capacity of FasL to bind Fas and to trigger the apoptosis of the corresponding cells.

In a particular embodiment, Fas activators of the present invention preferably include the FasL ligand or any functional fragment or derivative thereof. In one embodiment, Fas activators for use in the present invention is a Fas receptor agonist.

In a particular embodiment, Fas activators of the present invention preferably include the Fas receptor agonist APOOIO (TopoTarget, Copenhagen, Denmark), which is a recombinant, soluble, hexameric fusion protein consisting of three human Fas ligand (FasL) extracellular domains fused to the dimerforming collagen domain of human adiponectin with potential pro-apoptotic and antineoplastic activities. Fas receptor agonist APOOIO activates the Fas receptor, resulting in caspase dependent apoptosis in susceptible tumor cell populations (Verbrugge et al., 2009). In a particular embodiment, Fas activators of the present invention preferably include the Fas-agonist Mega FasL (AdipoGen). Further, additional Fas activators of the present invention preferably include Fas agonist peptides disclosed in U.S. Pat. Nos. 6,001,962 and 6,846,637.

In one embodiment, the agent of the invention is a preventive and/or therapeutic agent. In a particular embodiment, the agent of the invention is a therapeutic agent.

Within the meaning of the invention, by "inflammation", it is meant, as defined in Dorland's Medical Dictionary, "a localized protective response, elicited by injury or destruction of tissues, which serves to destroy, dilute or wall off both the injurious agent and the injured tissue". It is characterized by fenestration of the microvasculature, leakage of the elements of blood into the interstitial spaces, and migration of leukocytes into the inflamed tissue. On a macroscopic level, this is usually accompanied by the familiar clinical signs of erythema, edema, hyperalgesia (tenderness), and pain.

In one embodiment, the agent according to the invention is for use in the treatment of inflammation, wherein said inflammation is selected from the group comprising age-related macular degeneration (AMD), retinitis pigmentosa, Parkinson's disease, multiple sclerosis, Alzheimer's disease, obesity, atherosclerosis, allergies, ankylosing spondylitis, arthritis (osteoarthritis, rheumatoid arthritis, or psoriatic arthritis), asthma, graft versus host disease, peritonitis, Crohn's disease, colitis, dermatitis, diverticulitis, fibromyalgia, hepatitis, irritable bowel syndrome, systemic lupus erythematous, nephritis, and ulcerative colitis.

In one embodiment, the inflammation of the invention is an acute inflammation. In another embodiment, the inflammation of the invention is a chronic inflammation.

In one embodiment, the inflammation of the invention is a non-resolving inflammation. In one embodiment, the inflammation of the invention is a low-grade chronic inflammation. In one embodiment, the inflammation of the invention is a non-resolving and low-grade chronic inflammation.

In one embodiment, the inflammation of the invention is a non-resolving and low-grade chronic inflammation selected from the group comprising age-related diseases such as age-related macular degeneration (AMD) and age-related maculopathy (ARM); metabolic diseases, such as obesity and atherosclerosis; neurodegenerative diseases and cancers. In one embodiment, the non-resolving and low-grade chronic inflammation of the invention is age-related macular degeneration (AMD).

In one embodiment, the preventive and/or therapeutic agent of the invention is for use in the treatment of inflammation associated with mononuclear phagocytes accumulation.

Mononuclear phagocytes (MPs) comprise a family of cells that include microglial cells (MCs), monocytes (Mos) and macrophages (Mφs). Inflammation associated with mononuclear phagocytes accumulation includes, but is not limited to, retinal inflammation, such as age-related macular degeneration (AMD) age-related maculopathy (ARM) or retinitis pigmentosa; neurodegenerative diseases, such as Parkinson's disease, multiple sclerosis or Alzheimer's disease; metabolic disorders, such as obesity or atherosclerosis; allergies; ankylosing spondylitis; arthritis, such as osteoarthritis, rheumatoid arthritis, or psoriatic arthritis; asthma, graft versus host disease; peritonitis, Crohn's disease; colitis; dermatitis; diverticulitis; fibromyalgia; hepatitis; irritable bowel syndrome; systemic lupus erythematous; nephritis; and ulcerative colitis. In one embodiment the inflammation according to the invention is peritonitis.

In one embodiment, the inflammation according to the invention is selected from the group comprising retinal inflammation, such as age-related macular degeneration (AMD), retinitis pigmentosa or age-related maculopathy; neurodegenerative diseases, such as Parkinson's disease, multiple sclerosis or Alzheimer's disease; metabolic disorders, such as obesity or atherosclerosis.

In one embodiment, the inflammation according to the invention is an age-related disease selected from the group comprising AMD, age-related maculopathy, retinitis pigmentosa, atherosclerosis, and neurodegenerative diseases such as Parkinson's disease, multiple sclerosis or Alzheimer's disease.

In one embodiment, the inflammatory disease of the invention is not a cancer or a tumor. The retina is especially vulnerable to immunopathogenic damage as it has very limited regenerative capacities, but it is particularly protected from direct infection (sclera, eye lids), but also from blood-born microbial invasion (blood-tissue barrier). Additionally, this tissue is a site of "immune privilege", which contributes to itd protection against inflammation-mediated injury. Factors that participate in immune privilege include the lack of DCs and a lymphatic drainage system (e.g. eye and brain) through which antigen-presenting cells migrate to the lymph nodes, the lack of blood vessels through which effector cells infiltrate the tissue (cornea, subretinal space), and locally produced factors that induce immune tolerance. Importantly, this privilege is also mediated by tonic inhibitory signals in the retina that set the threshold for activation high and the particularly efficient clearance of infiltrating inflammatory cells (immunosuppressive microenvironment) compared to non-immune privileged tissues (Streilein et al., Vision Res. 2002, 42:487-495). In that way, potential antigen-presenting cells and effector cells (lymphocytes, macrophages) can be neutralized before they develop cytotoxicity.

In one embodiment, the inflammation according to the invention is a non-autoimmune inflammation. Examples of non-autoimmune inflammatory diseases include, but are not limited to, renal, liver and lung inflammation, atherosclerosis and metabolic syndrome, Behcets disease and endometriosis.

In one embodiment, the inflammation according to the invention is an autoimmune inflammation. Examples of autoimmune inflammatory diseases include, but are not limited to, rheumatoid arthritis, systemic lupus erythematosus, celiac sprue disease, scleroderma, psoriasis, inflammatory bowel diseases, and Sjögren's syndrome.

In one embodiment, the inflammation according to the invention is an ocular inflammation. As used herein, an ocular inflammatory disease is an inflammation affecting any part of the eye or surrounding tissue. Accordingly, inflammation developing in the eye(s), or in the optic nerve, blood vessels, muscles or other tissues that surround the eye, the resulting illness is an ocular inflammatory disease.

In one embodiment, the ocular inflammation is selected from the group comprising or consisting of age-related macular degeneration (AMD), retinitis pigmentosa, age-related maculopathy (ARM), uveitis, scleritis, episcleritis, optic neuritis, keratitis, orbital pseudotumor, retinal vasculitis, and chronic conjunctivitis.

In one embodiment, the inflammation according to the invention is not an ocular inflammation.

In one embodiment, the inflammation according to the invention is a retinal inflammation.

Within the meaning of the invention, by "retinal inflammation", it is meant an inflammation of the subretinal space mediated by mononuclear phagocytes. In an embodiment, the retinal inflammation of the invention comprises age-related macular degeneration (AMD), age-related maculopathy and retinitis pigmentosa.

In one embodiment, the agent of the invention is for use in the treatment of age-related macular degeneration. In a particular embodiment, the age-related macular degeneration comprises atrophic (or dry) AMD and neovascular (or wet) AMD.

In one embodiment, the preventive and/or therapeutic agent of the invention is for use in the treatment of atrophic AMD. In another embodiment, the preventive and/or therapeutic agent of the invention is for use in the treatment of neovascular AMD.

In one embodiment, the AMD according to the invention is at an early stage. Early stage is characterized by accumulation in and around the macula of extracellular deposits called drusen, associated with pigmented spots (pigmentary epithelium alterations).

In another embodiment, the AMD according to the invention is at late stage. Late stage is characterized by uni- or bilateral complications. Late stage AMD may be atrophic AMD or wet AMD. In a particular embodiment, the AMD is a late stage of the dry form of AMD (also named geographic AMD).

In one embodiment, the agent of the invention is for use in the treatment of age-related maculopathy (ARM). In one embodiment, the ARM is early ARM. In another embodiment, the ARM is late ARM.

In one embodiment, the agent of the invention is for use in the treatment of retinitis pigmentosa.

In one embodiment, the subject is affected by inflammation, preferably by an inflammation associated with mononuclear phagocytes accumulation. In a particular embodiment, the subject is affected by a retinal inflammation. In a preferred embodiment, the subject is affected by age-related macular degeneration (AMD), age-related maculopathy (ARM) or retinitis pigmentosa.

In one embodiment, the subject is affected by early stage AMD. In another embodiment, the subject is affected by late stage AMD. In one embodiment, the subject is affected by choroidal neovascularization AMD ("wet" AMD). In another embodiment, the subject is affected by geographic atrophy "dry" AMD).

In one embodiment, the subject is affected by early stage ARM. In another embodiment, the subject is affected by late stage ARM.

In another embodiment, the subject is susceptible to develop inflammation, i.e. to develop mononuclear phagocytes accumulation in a particular embodiment, the subject is at risk of developing retinal inflammation. In a preferred embodiment, the subject is at risk of developing AMD, ARM or retinitis pigmentosa.

Examples of risks of developing AMD and ARM include, but are not limited to, heredity, lifestyle such as smoking, sun exposure or poorly balanced diet, age, excessive blood concentration of cholesterol, high blood pressure, and the like.

In one embodiment, the subject of the invention is elderly. As used herein, the term "elderly" means that the subject is at least 50 years old, at least 55, 60, 65, 70, 75, 80, 85 or 90 years old.

In a particular embodiment, the subject is at risk of developing AMD due to the presence of the SNP rs11200638 located within the HTRA1 promoter on the human chromosome 10q26. The SNP rs11200638 is associated with a 10-fold increased risk of wet age related macular degeneration in Japanese and Caucasian populations. The genotype at highest risk is (A;A).

In one embodiment, the subject has not yet been treated with another treatment for inflammation, preferably AMD, ARM or retinitis pigmentosa. In another embodiment, the subject has already been treated with another treatment for inflammation, preferably AMD, ARM or retinitis pigmentosa.

The present invention also relates to a composition comprising at least one agent activating CD47 as described hereinabove. In one embodiment, the composition of the invention comprises at least one agent activating CD47 for use in the treatment of inflammation.

In one embodiment, the composition is used for treating (or for use in treating) inflammation.

In one embodiment, the composition of the invention comprises at least one agent directly activating CD47 and at least one agent indirectly activating CD47. In a particular embodiment, the composition of the invention comprises an agent activating CD47 and an agent activating Fas.

Another object of the invention is a pharmaceutical composition comprising at least one of the agent of the invention as described hereinabove and at least one pharmaceutically acceptable excipient.

Pharmaceutically acceptable excipients that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (for example sodium carboxymethylcellulose), polyethylene glycol, polyacrylates, waxes, polyethylene-polyoxypropylene-block polymers, polyethylene glycol and wool fat.

The invention further relates to a medicament comprising at least one agent, a composition or a pharmaceutical composition of the present invention.

In one embodiment, the composition, the pharmaceutical composition or the medicament of the invention is used for treating (or for use in treating) inflammation, preferably AMD.

Preferably, the composition, the pharmaceutical composition or the medicament of the invention comprises a therapeutically effective amount of the agent of the invention.

In one embodiment, the composition, the pharmaceutical composition or the medicament of the invention further comprises an additional preventive and/or therapeutic agent. According to one embodiment, said additional preventive and/or therapeutic agent is another agent for treating inflammation, in particular AMD.

It will be understood that the total daily usage of the compound of the invention, composition, pharmaceutical composition and medicament of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from about 10 to about 10000 mg per adult per day, preferably 100 to about 5000, more preferably from about 200 to about 2000 mg per adult per day. Preferably, the compositions contain 10, 50, 100, 250, 500, 1000 and 2,000 mg of the active ingredient for the symptomatic adjustment of the dosage to the patient to be treated. A medicament typically contains from about 10 to about 10000 mg of the active ingredient, preferably 5 to about 5000, more preferably from about 10 to about 2000 mg of the active ingredient. An effective amount of the drug is ordinarily supplied at a dosage level from 0.01 mg/kg to about 100 mg/kg of body weight per day, preferably from about 0.05 mg/kg to 40 mg/kg of body weight per day, more preferably from about 0.1 mg/kg to 20 mg/kg of body weight per day more preferably from about 0.2, mg/kg to 1 mg/kg of body weight per day.

In one embodiment, the therapeutically effective amount ranges from about 10 to about 10000 mg/ml of the composition, pharmaceutical composition or medicament of the invention, preferably 100 to about 5000 mg/ml, more preferably from about 200 to about 2000 mg/ml of the composition, pharmaceutical composition or medicament of the invention.

In one embodiment, the therapeutically effective amount ranges from about 10 to about 10000 mg/g of the composition, pharmaceutical composition or medicament of the invention, preferably 100 to about 5000 mg/g, more preferably from about 200 to about 2000 mg/g of the composition, pharmaceutical composition or medicament of the invention.

In one embodiment, the therapeutically effective amount ranges from about 10 to about 10000 mg/ml of the composition, pharmaceutical composition or medicament of the invention, preferably 5 to about 5000 mg/ml, more preferably from about 10 to about 2000 mg/ml, more preferably from about 20 to about 1000 mg/ml of the composition, pharmaceutical composition or medicament of the invention.

In one embodiment, the therapeutically effective amount ranges from about 10 to about 10000 mg/g of the composition, pharmaceutical composition or medicament of the invention, preferably 5 to about 5000 mg/g, more preferably from about 10 to about 2000 mg/g more preferably from about 20 to about 1000 mg/g of the composition, pharmaceutical composition or medicament of the invention.

In an embodiment of the invention, the preventive and/or therapeutic agent comprises a CD47 activator in a concentration of from about 5 mg/mL to about 500 mg/mL, from about 5 mg/mL to about 100 mg/mL, from about 5 mg/mL to about 10 mg/mL.

In an embodiment of the invention, the preventive and/or therapeutic agent comprises a CD47 activator in a concentration of from about 0.1 µM to about 1000 µM, preferably from about 1 µM to about 750 more preferably from about 5 µm to about 600 µM, even more preferably from about 10 µM and about 500 µM.

In another embodiment of the invention, the preventive and/or therapeutic agent comprises a CD47 activator in a concentration from about 1 µg/mL to about 1 mg/mL, from about 1 µg/mL to about 500 µg/mL, about 1 µg/mL to about 100 µg/mL.

In another embodiment of the invention, the preventive and/or therapeutic agent comprises a CD47 activator in an intraocular concentration of about 1 to about 10 µg/mL of human intraocular liquid, preferably about 5 µg/mL of human intraocular liquid.

For use in administration to a subject, the composition will be formulated for administration to the subject. The compositions of the present invention may be administered orally, parenterally, topically, by inhalation spray, rectally, nasally, buccally, vaginally or via an implanted reservoir. The term administration used herein includes subcutaneous, intravenous, intramuscular, intraocular, intra-articular, intra-synovial, intrasternal, intrathecal, intrahepatic, intralesional and intracranial injection or infusion techniques.

In one embodiment, the composition, pharmaceutical composition, or medicament of the invention is in a form adapted for oral administration.

Examples of forms adapted for oral administration include, but are not limited to, tablets, orodispersing/oro-dispersing tablets, effervescent tablets, powders, granules, pills (including sugarcoated pills), dragees, capsules (including soft gelatin capsules), syrups, liquids, gels or other drinkable solutions, suspensions, slurries, linosomal, forms and the like.

In one embodiment, the composition, pharmaceutical composition, or medicament of the invention comprises one or more pharmaceutical acceptable carrier for a formulation adapted for oral administration.

In one embodiment, the composition, pharmaceutical composition, medicament of the invention of the invention is in a form adapted for topical administration.

Examples of forms adapted for topical administration include, but are not limited to, liquid, paste or solid compositions, and more particularly in form of aqueous solutions, drops, eye drops, ophthalmic solutions, dispersions, sprays, microcapsules, micro- or nanoparticles, polymeric patch, or controlled-release patch. In a preferred embodiment, the composition, pharmaceutical composition, medicament of the invention of the invention is in the form of eye drops.

In one embodiment, the composition, pharmaceutical composition, or medicament of the invention is in a form adapted for injection, such as, for example, for intraocular, intramuscular, subcutaneous, intradermal transdermal or intravenous injection or infusion.

Examples of forms adapted for injection include, but are not limited to, solutions, such as, for example, sterile aqueous solutions, dispersions, emulsions, suspensions, solid forms suitable for using to prepare solutions or suspensions upon the addition of a liquid prior to use, such as, for example, powder, liposomal forms and the like.

Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid or other dosage forms may also be used for the purposes of formulation.

In a particular embodiment, the composition, pharmaceutical composition, or medicament of the invention is in a form adapted for intraocular administration, more preferably intraocular injection.

Within the meaning of the invention, by "intraocular administration" it is meant an injection of the agent directly in the interior of the eye, wherein the interior of the eye means any area located within the eyeball, and which generally includes, but is not limited to, any functional (e.g. for vision) or structural tissues found within the eyeball, or tissues or cellular layers that partially or completely line the interior of the eyeball. Specific examples of such areas include the anterior chamber, the posterior chamber, the vitreous cavity, the choroid, the macula, and the retina, and blood vessels and nerves which vascularize or innervate a posterior ocular region or site. In one embodiment, interior of the eye means the posterior segment of the eye, including the posterior chamber, the vitreous cavity, the choroid, the macula, and the retina, and blood vessels and nerves which vascularize or innervate a posterior ocular region or site. According to this embodiment, the intraocular administration refers to an administration within the posterior segment of the eye, preferably within the vitreous, and the intraocular administration is preferably an intravitreal injection.

In one embodiment, the composition, pharmaceutical composition, or medicament of the invention comprises one or more pharmaceutical acceptable carrier for a formulation adapted for injection.

In one embodiment, the composition, pharmaceutical composition, or medicament of the invention is administered to the subject in need thereof at least once a day. For example, the composition, pharmaceutical composition, or medicament of the invention may be administered once a day, twice a day, or three times a day. In a preferred embodiment, the composition, pharmaceutical composition, or medicament of the invention is administered to the subject in need thereof once a day. In another embodiment, the composition, pharmaceutical composition, or medicament of the invention is administered to the subject in need thereof at least once a week. For example, the composition, pharmaceutical composition, or medicament of the invention may be administered once a week, twice a week, three times a week, four times a week or up to seven times a week.

In another embodiment, the composition, pharmaceutical composition, or medicament of the invention is administered to the subject in need thereof once a month, two times a month, every two months, every two or three month, two times a year or once a year.

The present invention further concerns a method of treating inflammation in a subject in need thereof comprising administering to said subject a therapeutically effective amount of the agent of the invention.

In one embodiment, the method of the invention is for treating inflammation associated with mononuclear phagocytes accumulation. In a preferred embodiment, the method of the invention is for treating age-related macular degeneration.

In one embodiment, the composition, pharmaceutical composition or medicament of the invention is administered to the subject.

Another object of the present invention is a method for inhibiting CD47 activity in a subject in need thereof, comprising administering to the subject an effective amount of the agent of the invention.

Another object of the present invention is a method of eliminating mononuclear phagocytes accumulation in a subject in need thereof comprising administering said subject a therapeutically effective amount of the preventive and/or therapeutic agent as described hereinabove.

Another object of the present invention is a method of eliminating mononuclear phagocytes accumulation, thereby treating inflammation associated with mononuclear phagocytes accumulation in a subject in need thereof comprising administering to said subject a therapeutically effective amount of the preventive and/or therapeutic agent as described hereinabove.

The present invention also relates to a kit comprising at least one agent, a pharmaceutical composition or a medicament according to the invention.

In one embodiment, the kit of the invention further comprises means to administer the agent, the pharmaceutical composition or the medicament to a subject in need thereof.

In one embodiment, the kit of the invention further comprises instructions for the administration of the agent, the pharmaceutical composition or the medicament to said subject.

In one embodiment, the kit of the invention is a kit of parts, wherein the first part comprises at least one agent activating CD47 according to the invention, and wherein a second part comprises at least another agent activating CD47 according to the invention. In a particular embodiment, the kit of the invention is a kit of parts, wherein the first part comprises at least one agent directly activating CD47 according to the invention and at least one agent indirectly activating CD47 according to the invention. In a preferred embodiment, the kit of the invention is a kit of parts, wherein the first part comprises an agent activating CD47 and an agent activating Fas according to the invention.

In another embodiment, the kit of the invention comprises two parts wherein the first part comprises the at least one agent, pharmaceutical composition or medicament according to the invention, and wherein the second part comprises an additional preventive and/or therapeutic agent. According to one embodiment, said additional preventive and/or therapeutic agent is another agent for treating inflammation, in particular AMD.

In one embodiment, the components of the kit of parts of the invention may be administered separately, sequentially, simultaneously, concurrently or chronologically staggered.

In one embodiment, the kit of the invention is used for treating (or for use in treating) inflammation.

In one embodiment, the part of the kit of part comprising the additional preventive and/or therapeutic agent is in a form adapted to the same administration route than the at least one agent, pharmaceutical composition or medicament of the invention. In another embodiment, the part of the kit of part comprising the additional preventive and/or therapeutic agent is in a form adapted to another administration route than the at least one agent, pharmaceutical composition or medicament of the invention.

BRIEF DESCRIPTION OF THE DRAWINGS

FIG. 4 is a set of histograms showing the survival of monocytes (Mo) in co-culture with retinal pigment epithelium cells (RPE), a model of subretinal immune-suppressivity: (i) HTRA-1 disrupts RPE-associated immune-suppressivity; (ii) simultaneous treatment with the CD47 agonist TSP1 and the FAS agonist MegaFasL restores the immune-suppressivity after HTRA1 has been removed; (iii) the CD47 agonist peptide restores HTRA-1-induced immunosuppressivity disruption in the presence of HTRA-1. (A)

Number of CFSE$^+$Mo (right panel) and OTX-2 positive RPE cells (left panel) after various time points of Mo monoculture (undisrupted lines) and Mo/RPE co-culture (dotted lines) with and without HTRA-1; (B) Number of CFSE$^+$Mo after 24 h of co-culture with HTRA-1 followed by 24 hr control or 24 h with TSP-1 and MegaFasL (n=3; Anova/Dunnets *p=0.0018)); (C) Number of CFSE-+Mo after 24 h of co-culture with HTRA-1 and simultaneous stimulation of the control peptide 4NGG or the CD47-stimulating peptide PKT16 (n=3; ANOVADunetts *p=0.0286). (D) Number of PU1$^+$Mo after 48 h of co-culture with HTRA-1 and simultaneous stimulation of the control peptide 4NGG or the CD47-stimulating peptide 4NK1 or PKT16 at the indicated concentrations (n=8; ANOVADunns compared to the control HTRA1 without peptides *p<0,0001). (E) Number of PU1$^+$Mo after 48 h of co-culture with HTRA-1 and simultaneous stimulation of the control peptide 4NGG or the CD47-stimulating peptide 4NK1 or the 4N1K-GGGGGGGG-4N1K bi peptide at the indicated concentrations (n=8; ANOVADunns compared to the control HTRA1 without peptides *p<0,0001).

Figure 5:
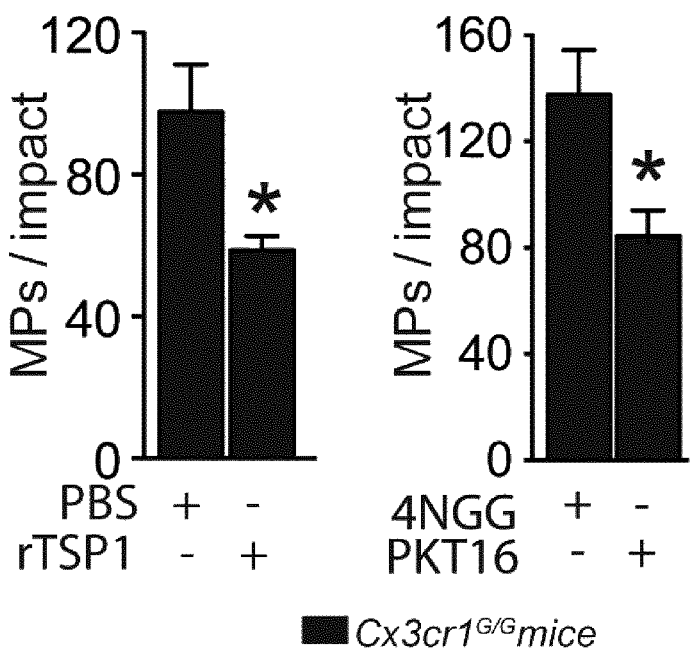

FIG. 5 is a set of histograms showing the elimination of subretinal mononuclear phagocytes in laser-injured Cx3cr1$^{GFP/GFP}$ mice. Quantification subretinal IRA-1$^+$ MPs on the RPE counted at a distance of 0-500 μm from CD102$^+$ CNV 10 days after the laser-injury in 2 month-old Cx3cr1$^{GFP/GFP}$ mice injected at day 4 and day 7 with 2 μl of PBS, recombinant human TSP-1 (10 μg/ml), the 4NGG control peptide or the PKHB1 CD47-activating peptide (200 μM) (n=20-25 impacts, Mann Whitney *p<0,0001).

Figure 6:
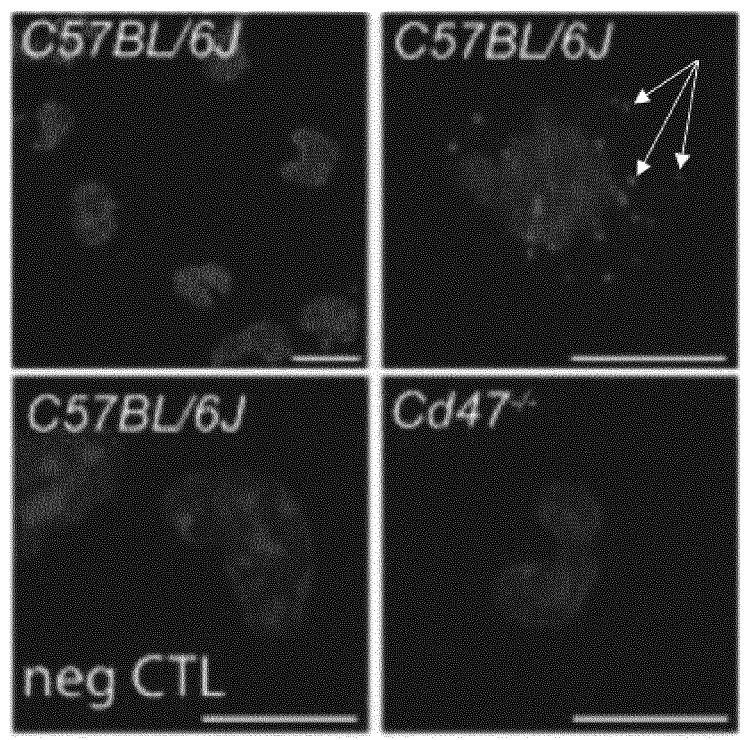

FIG. 6 is a set of photographs showing confocal micrographs of CD 11b-CD47 complexes (white dots marked by arrows) detected by proximity ligation assay on freshly harvested Mo-derived Mφ 1 day after thioglycolate injection in WT C57BL6/J (top right) and. Cd47$^{-/-}$ mice (bottom right). Negative controls correspond to WT C57BL6/J mice not induced for peritonitis (left). Hoechst was used for nuclear stain (grey; negative control: omitting the primary antibodies; the experiment was repeated three times with similar results). negCTL=negative control, scale bar=10 μm.

Figure 7:
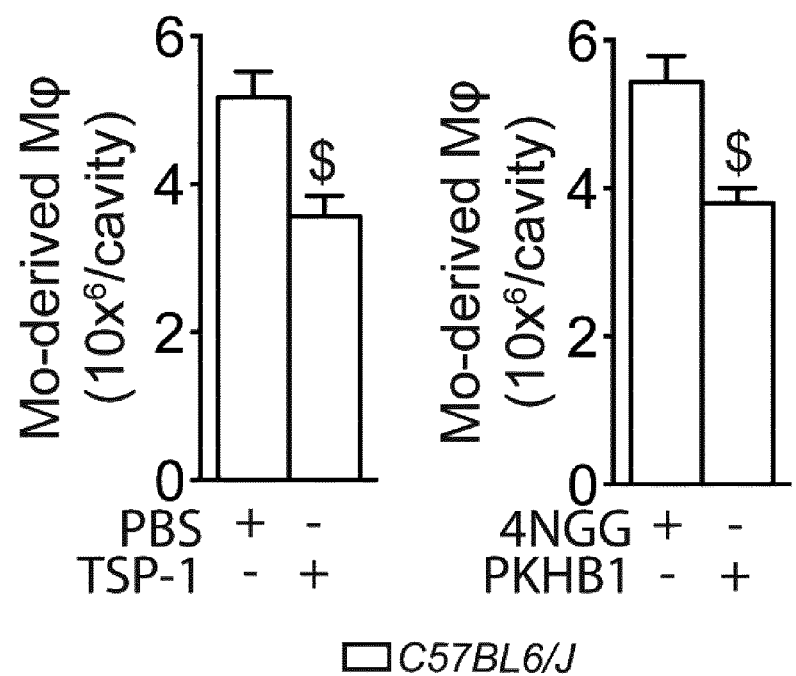

FIG. 7 is a set of histograms showing quantification of CD115$^+$ F4/80$^+$ICAM-2$^{lo}$ Mo-derived Mφ in exudates of WT C57BL6/J mice at day 2 after mice were injected with PBS or rTSP-1 (Mann Whitney $^\$$p=0,0048); or control peptide 4NGG or CD47-activating peptide PKHB1 (Mann Whitney $^\$$p=0,0087) at day 1.

EXAMPLES

The present invention will be better understood with reference to the following examples. These examples are intended to representative of specific embodiments of the invention, and are not intended as limiting the scope of the invention.

Materials and Methods

Western Blot, Reverse transcription and real-time polymerase chain reaction and ELISA WB analysis was performed using a monoclonal anti-TSP1 antibody (Abcam), as previously described (Houssier et al., PLoS Med. 2008, 5:e39). RT-PCRs primers were ordered from Taqman, reference: Hs01016151_m1.

Microglial Cell Preparations

Microglial cells were prepared from PBS-perfused mice. After dissociation of brain or retina with Neural Dissociation Kit Papain (miltenyi Biotech), 70 μm filtered cell suspensions were washed and resuspended in 75% isotonic Percoll (Percoll Plus, GE Healthcare), overlayed with 25% Percoll and PBS. Cells were centrifuged at 1000 g for 30 min at 4+ C. The ring at the 75%/25% interface was collected, washed with PBS and centrifuged.

RPE-Mo Coculture

Monocytes

In accordance with the Declaration of Helsinki, volunteers provided written and informed consent for the human monocyte expression studies, which were approved by the Centre national d'ophthalmologic des Quinze-Vinet hospital (Paris, France) ethics committees (no. 913572). PBMCs were isolated from heparinized venous blood from healthy volunteer individuals by 1-step centrifugation on a Ficoll Paque layer (GE Healthcare) and sorted with EasySep Human Monocyte Enrichment Cocktail without CD16 Depletion Kit (StemCells Technology). Mouse peritoneal macrophages, bone marrow-derived monocytes and photoreceptor outer segment (POS) isolation (all in serum-free X-Vivo 15 medium) were performed as previously described (Sennlaub et al, EMBO Mol Med. 2013, 5:1775-1793). For co-culture experiments the mononuclear monocytes were either stained using CellTrace™ CFSE (Life Technologies®) and then washed three times or they were identified by PU1 immunohistochemistry, a MP-specific transcription factor not expressed in RPE.

Primary RPE Culture

Fresh pig eyes were obtained from the slaughter house 2-3 hours after enucleation. They were cleaned of surrounding tissue and immersed briefly in antiseptic solution (Pursept®). The anterior part of the eye was removed, as the lens, vitreous and vitreous. The posterior segments were washed 2 times with PBS (Phosphate Buffered Saline) and then incubated at 37° C. in the presence of 0.25% trypsin, to detach the RPE cells. After 1 h incubation, the trypsin solution was removed and the cells recovered in Dulbecco's Modified Eagle's Medium (DMEM) supplemented with 20% fetal calf serum (FCS) decomplemented and in the presence of antibiotics (1% penicillin/Streptomycin). The cells were washed several times and then incubated at 37° C. in culture dishes. Three days after the culturing, these cells were again incubated with by 0.25% trypsin, washed, and seeded into 48 wells culture plates (Grenier®) at a density of 150,000 cells/culture well (300,000 cells/L or 500 μL/well). Cell confluence was obtained after 4 days of incubation at 37° C. with optimum cell characteristics (squamous cells, well pigmented). To avoid the aging of these primary cell cultures, all the experiments were conducted between the 5th and 7th day after seeding the culture plates.

Monocytes RPE Co-Culture

The culture medium of RPE cells was changed the day before the co-culture with DMEM without FCS (DMEM+1% Penicillin/Streptomycin only). Monocytes were plated onto the wells in the presence or absence of RPE cells at a concentration of 200,000 cells/culture well in a 48-well plate.

Part of co-culture well was brought into contact with 1 ng/ml of Lipopolysaccharide (LPS) from *E. coli* or recombinant HTRA1 (R & D, 5 μg/ml), to simulate a systemic inflammatory activation (LPS) or microenvironment similar to AMD (increase HTRA1) (see above). After 24 hours incubation at 37° C., the cells were fixed with 4% paraformaldehyde (PAF) for 30 minutes at 4° C.

Immunohistochemistry

RPE cells were permeabilized, after washing PAF 4%, with a solution of PBS-0.1% Triton-Citrate 0.1%. Nonspecific immunogenic sites were blocked with PBS-0.1% Triton-5% horse serum. After 1 hour, the blocking solution was removed and the cells were placed in presence of the with the primary antibodies (polyclonal rabbit anti-human PU.1, 1/200, LifeTechnologies; polyclonal goat anti-human OTX2, 1/500, R&D) diluted in PBS triton 0.1% and 1% horse serum and incubated at 4° C. for 12 h. After three washes with PBS, the secondary antibody coupled to a fluorochrome and diluted in PBS-0.1% Triton-1% horse serum was added along with DAPI (nuclear staining) and left for 1 hour at temperature ambient and then washed several times with PBS.

Reading and automated quantification by fluorescence microscopy reversed (Arrayscan®)

25 fields per well were analyzed Arrayscan® then the number of cells for each culture condition was counted directly by a computer protocol. All nuclei were labeled with DAPI, monocytes were marked in green 488 nm (Cell-Trace™ CFSE) or and RPE cells in far red 647 nm (recognition of anti-OTX2 primary antibody). For graphs where quantifications from several plates were pooled (FIGS. 4D and E) results were expressed as the percentage of the number of PU.1 or OTX2 positive cells normalized with the HTRA1 treated condition.

Digested TSP1 Liquid Chromatography-Tandem Mass Spectrometry (LC-MS/M)+Spectra Analysis Tryptic Digestion Proteins were submitted to reduction by incubation with 5 mM dithiotreitol in 50 mM ammonium bicarbonate (AmBic) for 30 min at 37° C., then alkylation with 15 mM iodoacetamide in 50 mM AmBic for 30 min, RT. Tryptic digestion was performed with a protein/enzyme ratio of 25/1 at 37° C. overnight in 50 mM AmBic.

Mass Spectrometry Analysis

Peptide mixtures were supplemented with formic acid to a final concentration of 0.1% and analyzed on a U3000 nanoLC (Thermo) coupled to an HCTultra ion trap (Bruker). Peptides were concentrated and desalted for 5 min on a precolumm RP-C18 (5 mm, 300 µm i.d., 100 Å, Thermo) with a mobile phase A (2% ACN/0.1% formic acid) at a flow rate of 20 µL/min then separated on an analytical column RP-C18 (15 cm, 75 µm i.d., 100 Å, Dionex) at a flow rate of 300 nL/min. Elution gradient was run from 2% to 10% of solvent B (95% ACN/0.1% formic acid) in 10 min then 10% to 35% B in 60 min and 35% to 50% B in 10 min. The ion trap was used in the positive mode with the selection of 8 precursors from each MS spectrum for fragmentation by collision induced dissociation (CID). Capillary voltage was set at 2 kV, Full scan spectra were acquired in the mass range 250 to 1600 m/z and MSMS spectra were acquired from 100 to 2800 m/z with singly charged ions exclusion, a dynamic exclusion of 30 sec and an isolation width of 4 Da. ICC smart target was set to 250000 and the target mass to 622 m/z.

Tryptic peptides were also analyzed by MALDI-TOF MS on an Autoflex speed (Bruker) in positive reflectron mode in the mass range 700-4000 m/z using α-Cyano-4-hydroxycinnamic acid as the matrix (0.9 mg/mL CHCA in 85% CAN, 0.1% TFA, 10 mM ammonium phosphate).

Protein Identification

For LC-MS/MS data analyses, raw data were processed using Data Analysis 3.4 (Bruker). Mgf files were generated with a maximum of 5000 compounds with a signal intensity threshold of 100000 (AU) and spectra deconvolution. Protein identification was performed with ProteinScape 2.1 (Bruker) using Mascot with SwissProt database (Jan. 4, 2015), Homos sapiens taxonomy (20203 entries). Trypsin was selected as the enzyme with 2 missed cleavages. Carbamidomethylation of Cys was set as a fixed modification and oxidation of Met as variable modifications. MS tolerance and MS/MS tolerance were set at 0.5 Da. A p value<0.05 was required for peptide validation. In addition, analyses were performed using semi-trypsin as the enzyme using the same parameters.

For MALDI-TOF data PMF analysis was run using BioTools 3.2 (Bruker) and Mascot with the following parameters: SwissProt database (Jan. 4, 2015), Homos sapiens taxonomy (20203 entries); trypsin or semi-trypsin as the enzyme; 1 missed cleavage; carbamidomethylation of Cys as a fixed modification and oxidation of Met as variable modifications; MS tolerance at 60 ppm and a p value<0.05 was required for protein validation.

Animals

Tsp $1^{-/-}$, CD47$^{-/-}$, CD36$^{-/-}$, and Cx3cr1$^{GFP/GFP}$-mice were purchased (Charles River Laboratories, Jackson laboratories). All mice were either negative or backcrossed to become negative (Tsp1$^{-/-}$) for the Crb1rd8, Pdc6brd1, and Gnat2cpfl3 mutations. Mice were housed in the animal facility under specific pathogen-free condition, in a 12/12 h light/dark (100-500 lux) cycle with water and normal diet food available ad libitum. All experimental protocols and procedures were approved by the local animal care ethics committee "Comité d'éthique en expérimentation animale Charles Darwin" (N° Ce5/2010/011, Ce5/2010/044, Ce5/2011/033).

PKT16 Synthesis

PKT16 was synthesized using a mixed solid/solution phase procedure. Briefly, 2-Chlorotritylchloride resin was previously swelled in strictly anhydrous $CH_2Cl_2$ for 2 h. Fmoc-Aa-OH (0.32 mmol) was coupled to 2-CTC resin (400 mg, loading=1.6 mmol/g) in the presence of diisopropyethylamine (DIPEA, 4 eq.) in $CH_2Cl_2$ (4 mL). The unreacted sites on the resin were capped by washing with a mixture of $CH_2Cl_2$/MeOH/DIPEA (7:2:1) followed by MeOH. After removal of the Fmoc-group using 20% piperidine in N,N-dimethylformamide (DMF), chain elongation was performed with standard Fmoc-protected amino acids (Bachem, Switzerland), using 20% piperidine/DMF for Fmoc deprotection, 2-(1H-benzotriazole-1-yl)-1,1,3,3-tetramethyluranium hexafluorophosphate/1-hydroxybenzotriazole (HBTU/HOBt) for activation, DIPEA as base and N-methyl-2-pyrrolidinone (NMP) as solvent. When assembly of the linear peptide chain was complete, additional MeOH wash was carried for final washing step (1×1 min, 1×15 min) in order to shrink the resin.

The peptide was cleaved from the resin by 2 times treatment with HFIP/$CH_2Cl_2$ cocktail (1:4, v/v) for 15 min each. The reaction mixture is filtered and the resin is sequentially rinsed with $CH_2Cl_2$ and MeOH. The filtrates are pooled and the solvents were subsequently evaporated under reduced pressure. At the end, the crude linear peptide was precipitated 3 times using dry-ice cold EtO2 and recovered after centrifugations (3×5 min, 7800 rpm) and drying (under nitrogen flow). The crude was purified by HPLC.

Laser-Injury Model

Laser-coagulations were performed with a 532 nm ophtalmological laser mounted on an operating microscope (Vitra Laser, 532 nm, 450 mW, 50 ms, and 250 µm): Intravitreal injections of 2 µl of HTRA1 and/or TSP1 were performed using glass capillaries (Eppendorf) and a micro injector. The 2 µl injection solution contained 50 µg/ml TSP1 and HTRA1, corresponding to an intraocular concentration of 5 µg/ml of each protein assuming their dilution by approximately 1/10th in the intra-ocular volume. In set of experiments Cx3cr1$^{GFP/GFP}$ mice, that develop exaggerated subretinal inflammation with age, after a light-challenge and after laser injury (Combadiere et al., J Clin Invest. 2007, 117:2920-2928; Levy et al., EMBO Mol Med. 2015, 7:211-226) were submitted to a laser-injury. A volume of 2 µl of a 100 µM solution of either PBS, recombinant TSP1 (10 µg/ml), the 4NGG control peptide or the CD47-activating peptide PKT16 (200 µM) was injected at day 4 (when MP infiltration is maximal) and day 7 after the injury and evaluated subretinal inflammation on flatmounted RPE/choroidal flatmounts at day 10.

Light Challenge Model

Two- to three-month-old mice were adapted to darkness for 6 hours, pupils dilated and exposed to green LED light (starting at 2 AM, 4500 Lux, JP Vezon equipements) for 4 days and subsequently kept in cyclic 12 h/12 h normal facility conditions as previously described (Sennlaub et al., EMBO Mol Med. 2013, 5:1775-1793). MP count was assessed at the end of light exposure or 10 (d14) later.

Choroidal and Retinal Flatmounts for Mononuclear Phagocytes Quantification

Eyes were enucleated, fixed in 4% PFA 30 minutes and sectioned at the limbus; the cornea and lens were discarded. The retinas were carefully peeled from the RPE/choroid/sclera. Retina and choroid were incubated with anti-IBA-1 (Wako chemicals) followed by secondary antibody anti-rabbit Alexa 488 (Molecular Probes) and Hoechst staining. Choroids and retinas were flatmounted and viewed with a fluorescence microscope DM5500B (Leica). IBA-1+ cells were counted on whole RPE/choroidal flatmounts and on the outer segment side of the retina.

Subretinal Adoptive MP Transfer and Clearance

According to Levy et al., (EMBO Mol Med. 2015, 7:211-226), brain microglia of the indicated mouse strains were sorted as describe above, labeled in 10 µM CFSE (Life Technologies), washed and resuspended in PBS, 12000 cells (4 µL) were injected using glass microcapillaries (Eppendorf) and a microinjector in the subretinal space of anesthetized 10-14 weeks old wildtype mice. A hole was pierced with the glass capillary prior to the subretinal injection to avoid intra-ocular pressure increase and to allow retinal detachment with 4 µL of solution. The subretinal injection was verified by fundoscopy. In specific experiments, cells were co-injected with recombinant human TSP1 (10 µg/ml, R&D Systems), Eyes were enucleated after 24 hours, fixed in PFA 4% 30 minutes and labeled with DAPI. Eyes with hemorrhages were discarded. CFSE+cells in the subretinal space were quantified on flatmounts on the RPE side of the retina and on the apical side of the RPE.

Thioglycollate Induced Peritonitis and Flow Cytometry

Mouse peritoneal exudate cells (PECs) were elicited by i.p. injection of 0,5 ml 3% thioglycollate (T9032, Sigma) into 10 weeks old male C57BL/6J and Cd47$^{-/-}$ mice. After 1 day, PECs were isolated by flushing of the peritoneum with ice-cold PBS, Mφs were negatively selected by magnetic sorting following the manufacturers protocol (EasySep Mouse Monocyte Enrichment Kit, Stemcell Technologies), resuspended in X-VIVO 15 medium (Lonza), and plated in Lab-Tek® Chamber Slide™ (Nunc®).

After 2 h at 37° C. in a 5% CO2 atmosphere, cells were rinsed with PBS fixed 10 minutes in 4% paraformaldehyde solution, rinsed and permeabilized by incubating cells 10 minutes in 0.1% Triton solution in PBS. Duolink® PLA assay was performed following the manufacturer's instructions (Sigma-Aldrich). In brief, rabbit anti-CD11b (ab75476, Abcam; 1:1000) and goat anti-C©47 (AF1866, R&D Systems; 1:1000) were incubated overnight at 4° C. Afterwards, anti-rabbit and anti-mouse oligonucleotides-labeled secondary antibodies (PLA probes) were incubated, followed by a ligase and polymerase reaction to amplify the signal. Images were taken on an Olympus FLUOVIEW FV1000 confocal laser-scanning microscope.

Statistical Analysis

Graph Pad 6 (GraphPad Software) was used for data analysis and graphic representation. All values are reported as mean +/− SEM. Statistical analysis was performed by one-way ANOVA followed by Bonferroni post-test (for multiple comparison) or Mann-Whitney U-test (2-group comparison) among means depending on the experimental design. The n- and P-values are indicated in the figure legends.

Example 1

TSP1 Mediates MP Elimination Via CD47

Figure 1:
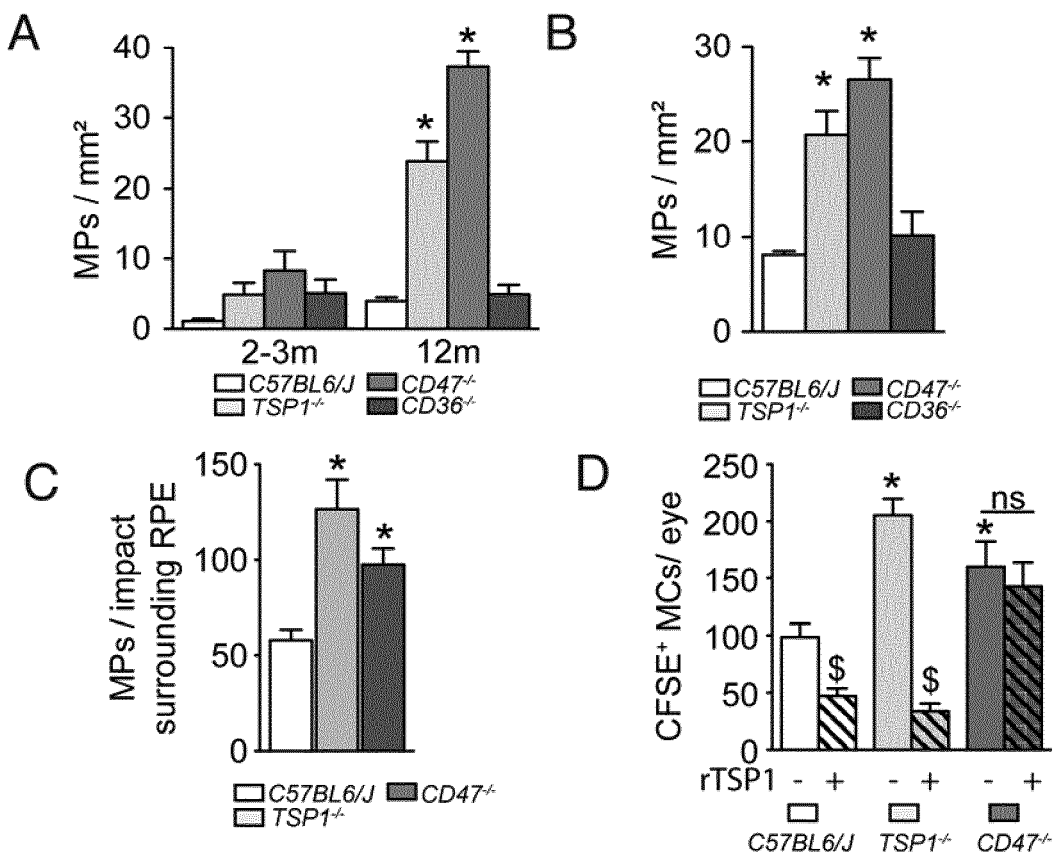
FIG. 1 is a set of histograms showing mononuclear phagocytes elimination mediated by TSP1 via CD47. (A) Quantification of subretinal IBA-1$^+$ mononuclear monocytes in 2-3 m- and 12m-old C57BL6/J wildtype, Tsp1$^{-/-}$, Cd47$^{-/-}$-mice, and Cd36$^{-/-}$-mice (n=6-9 per group, one-way Anova/Bonferroni test *p<0.0001 versus the strains 2-3 m group). (B) Quantification of subretinal IBA-1$^+$ mononuclear monocytes in 2-3 m-old C57BL6/J wildtype, Tsp1$^{-/-}$, Cd47$^{-/-}$-mice, and Cd36$^{-/-}$-mice after 4d of exposure to 4500 lux of constant green light (n=6-12/group Anova/Dunnet *p<0.0001 versus the control group). (C) Quantification of subretinal IBA-1$^-$ mononuclear monocytes on the RPE counted at a distance of 0-500 μm to CD102$^+$CNV 7 days after the laser-injury of 3 m-old mice of the indicated strains (n=9-21/group Anova/Dunnet *p<0,0001 versus the control group). (D) Quantification of CFSE microglial cells of the indicated strains, 24 h after adoptive transfer to C57BL6/J wildtype mice with and without recombinant TSP (10 μg/ml, n=8-16/group; one-way Anova/Bonferroni test *p<0.0001 versus C57BL6/J CSFE$^+$ microglial cells; $^$p<0.000 versus the same strains CSFE$^+$ microglial cells without TSP1).

TSP1 participates in subretinal mononuclear monocytes elimination, as Tsp1$^{-/-}$ mice display increased and prolonged subretinal inflammation after experimentally induced chorio-retinitis, light- and laser-induced injury (Wang et al., Arch Ophthalmol. 2012, 130:615-620; Ng et al., Invest Opthalmol. Vis Sci. 2009, 50:5472-5478; Chen et al., Am J Pathol, 2012, 180:235-245). The TSP1 receptor that mediates this effect is unknown. Quantification of subretinal IBA-1$^+$ mononuclear monocytes on retinal and RPE/choroidal-flatmounts of 2-3 month-old and 12 month-old mice revealed a significant age-related increase in subretinal mononuclear monocytes in Tsp1$^{-/-}$ and Cd.47$^{-/-}$-mice, but not in Cd36$^{-/-}$-mice compared to wildtype animals kept in the same conditions (FIG. 1A, all mice were backcrossed to eliminate the Crb1$^{rd8}$ gene and raised under 12-h light/12-h dark cycles at 100-500 lux at the cage level, with no additional cover in the cage).

Similarly, Tsp1$^{-/-}$ and Cd47$^{-/-}$-mice accumulated significantly more subretinal mononuclear monocytes after a four-day light-challenge and the mononuclear monocytes continued to accumulate after return for 10 additional days in normal light conditions (FIG. 1B, the intensity of our light-challenge model used herein was calibrated to induce subretinal inflammation in inflammation-prone Cx3cr1$^{GFP/GFP}$-mice but not in WT mice (Sennlaub et al., EMBO Mol Med. 2013, 5:1775-1793). In addition, subretinal IBA-1$^+$ mononuclear monocytes were significantly more numerous in Tsp1$^{-/-}$ and Cd47$^{-/-}$-mice seven days after a laser-impact (FIG. 1C).

These results suggested that TSP1 participates in subretinal MP elimination via its receptor CD47.

Adoptive transfer experiments in which CBE-labeled brain microglial cells from wildtype-, Tsp1$^{-/-}$, or Cd47$^{-/-}$-mice were subretinally injected into wildtype recipients. The evaluation of the subretinal microglial cells population on flatmounts after 24 h showed that Tsp1$^{-/-}$ and Cd47$^{-/-}$-microglial cells significantly resisted to elimination compared to wildtype microglial cells (FIG. 1D). Co-injected recombinant TSP1 very significantly accelerated the elimination of wiltype-microglial cells and reversed the phenotype of Tsp1$^{-/-}$-microglial cells but had no effect on Cd47$^{-/-}$-microglial cells, confirming that the interaction of TSP1 and CD47 mediates microglial cells elimination (FIG. 1D).

Taken together, these data show that TSP1 eliminates subretinal microglial cells via their CD47 receptor and that this interaction is physiologically important, as both TSP1- and CD47-deficient animals develop age-, light- and laser-induced subretinal mononuclear phargocytes accumulation. Interestingly, as CD36$^{-/-}$ did not share the Tsp1$^{-/-}$ phenotype of subretinal mononuclear phargocytes accumulation our data also suggests that CD36, nor TGFβ (which cannot be activated in the absence of CD36) are significantly involved in this mechanism.

Example 2

Figure 2:
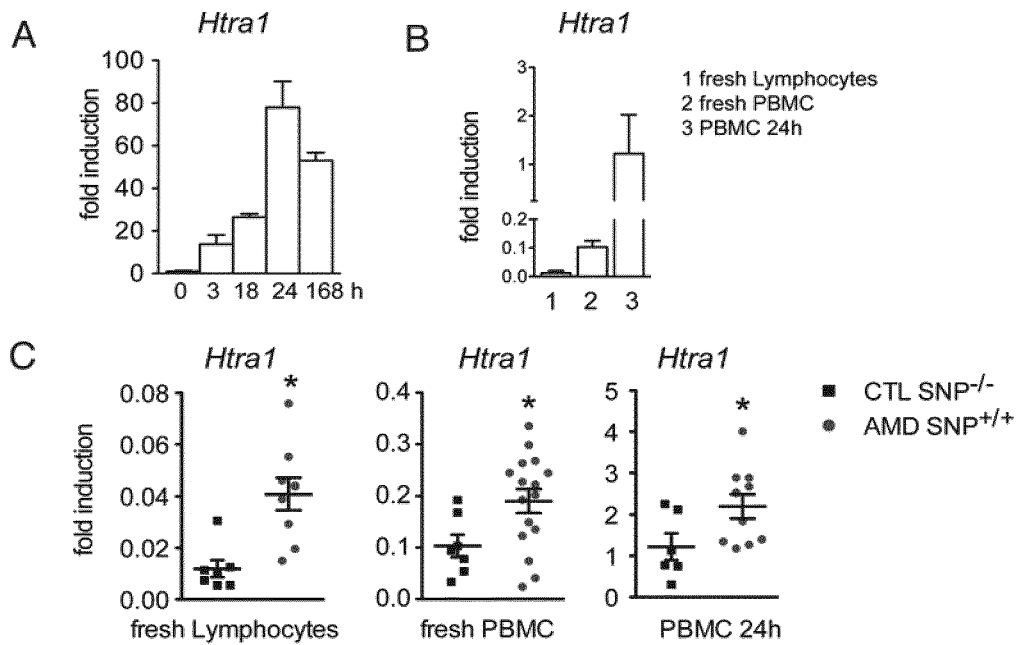
FIG. 2 is a set of graphs showing SNP rs11200638 and HTRA1 expression in leucocytes. (A) Quantitative RT-PCR of Htra1 mRNA normalized with Rps26 mRNA of monocytes isolated from blood of healthy human donors after the indicated times of culture in vitro (3 preparations gave similar results). (B) Quantitative RT-PCR of Htra1 mRNA normalized with Rps26 mRNA of healthy donor human blood lymphocytes, monocytes and monocytes after 24 h of culture (3 preparations gave similar results). (C) Quantitative RT-PCR of Htra1 mRNA normalized with Rps26 mRNA of fresh blood derived lymphocytes and monocytes, and after 24 h of monocyte culture of patients with wet AMD homozygeous for rs11200638 and age-matched control subjects without the polymorphism (n indicated in the scatter blot; Mann Whitney: fresh lymphocytes *p=0.0012; freshPBMC*p=0.0353; 24 h PBMC*p=0.0312). PBMC: peripheral blood monocyte.

The AMD-Associated SNP rs11200638 Significantly Increases HTRA1 Expression in Monocyte Derived Macrophages Numerous genetic association studies have shown that chromosome 10q26 is a major candidate region associated with AMD. The risk haplotype contains the SNP rs11200638 (Yang et al., Science. 2006, 314:992-993), which disrupts the CG pattern in a conserved CpG Island (sites of DNA methylation) of the high-temperature requirement A serine peptidase 1 (HTRA1) promoter. The SNP has been shown to remove epigenetic inhibition of HTRA1 transcription in lymphocytes (Yang et al., Science. 2006, 314:992-993). Contrary to macrophages that can express HTRA1 (Hou et al., Arthritis and rheumatism. 2013, 65:2835-2846), lymphocytes are however not present in significant numbers in the retina of AMD patients. To evaluate HTRA1 expression in monocyte derived macrophages, its expression in freshly purified $CD14^{-/-}$ peripheral blood monocytes (PBMC) from healthy donors cultured for different amounts of time was first analyzed. RT-PCR analysis of HTRA1 showed a fast and significant HTRA1 induction in early monocyte to macrophage differentiation that persisted at high levels for at least 168 h (7 days; FIG. 2A). RT-PCR analysis revealed that fresh PBMCs expressed 10× more Htra1 mRNA compared to fresh blood lymphocytes and that this expression increased by another factor of 10 after 24 h of PBMC culture (FIG. 2B). Quantitative RT-PCR of patients with wet AMD homozygeous for rs11200638 and age-matched control subjects without the polymorphism confirmed that rs11200638 is associated with significantly higher Htra1 mRNA levels in lymphocytes, but also more importantly in PBMCs and early PBMC-derived macrophages, as they express higher amounts of Htra1 and accumulate in AMD (FIG. 2C).

In summary, these data confirm that rs11200638 is associated with increased Htra1 transcription in lymphocytes and extends that observation to mononuclear monocytes that we showed accumulate in AMD and play a pathogenic role.

Example 3

HTRA1 Degrades TSP1

Figure 3:
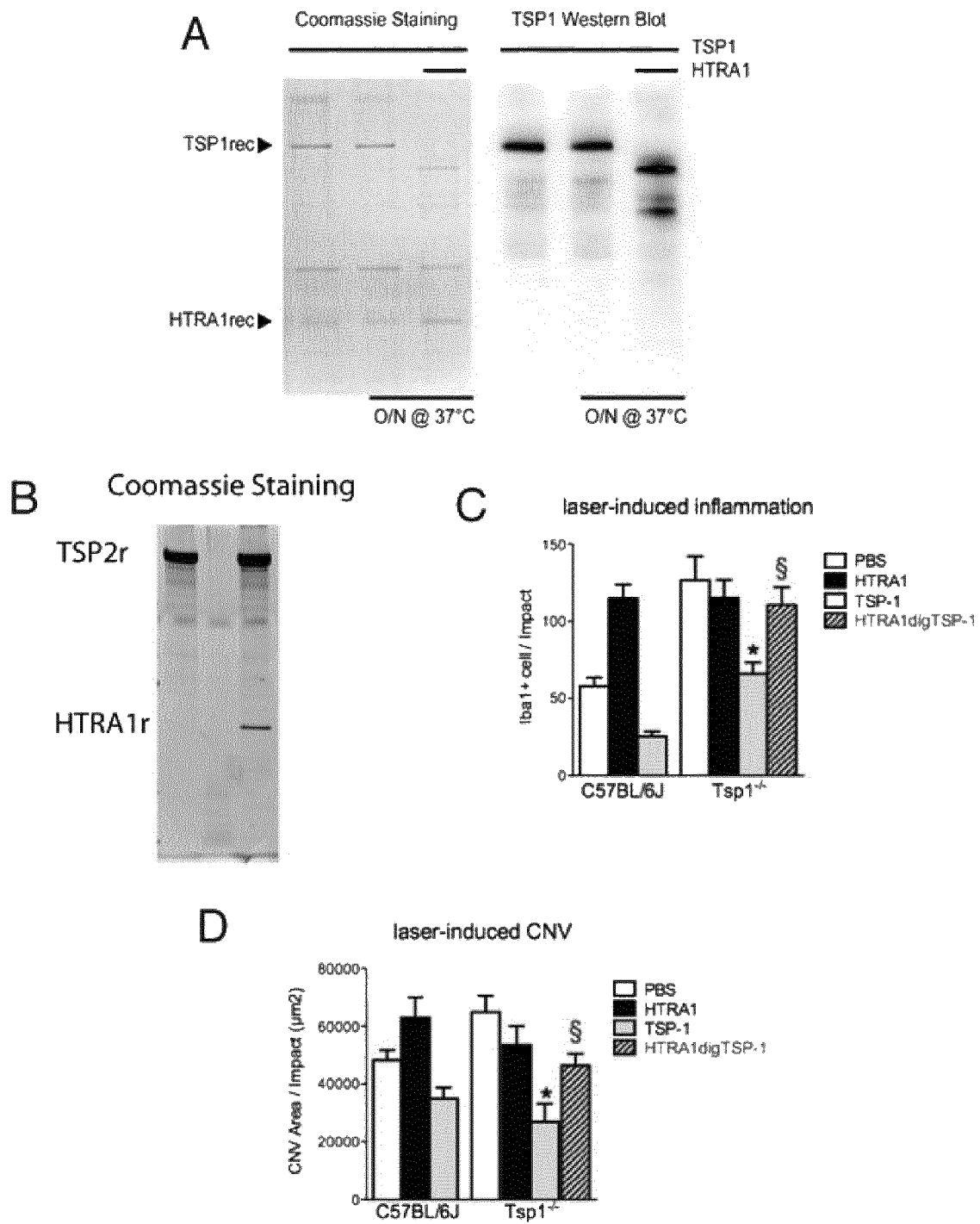
FIG. 3 shows TSP1 degradation mediated by HTRA1. (A) Coumassie staining and Western blot of recombinant TSP1 and recombinant TSP1 that had been co-incubated with recombinant HTRA1 at 37° C. (B) Coumassie staining and Western blot of recombinant TSP2 and recombinant TSP2 that had been co-incubated with recombinant HTRA1 at 37° C. (C) and (D) Quantification of (C) subretinal IBA-1$^+$ mononuclear monocytes on the RPE counted at a distance of 0-500 μm to CD102$^-$CNV and (D) area of CD102$^+$CNV 7 days after the laser-injury of 3 m-old mice of wildtype- and Tsp1$^{-/-}$-mice that received an intravitreal injection of (n=9-39/group; Mann Whitney *p=0.0013 PBS versus TSP1 injected Tsp1$^{-/-}$-mice; $^$p=0.0014 TSP1 versus rHTRA1-digested rTSP1 injected Tsp1$^{-/-}$-mice.

HTRA1 is a rather unselective protease and has been shown to degrade several proteins (An et al., Invest Ophthamol Vis Sci. 2010, 51:3379-3386). Interestingly, coomassie-staining of an electrophorese gel of recombinant TSP1. (rTSP1) that had been co-incubation at 37° C. for 24 h with recombinant HTRA1 (rHTRA1) revealed that HTRA1 degrades TSP1 (FIG. 3A). Western blot analysis of the proteins confirmed the disappearance of the whole sized TSP1 and the appearance of several smaller bands in the co-incubated condition (FIG. 3A). Coomassie-stained of electrophorese gels of recombinant TSP2/ rHTRA1 co-incubated proteins revealed no such degradation (FIG. 3B). Next the functionality of rTSP1 and HTRA1-digested TSP1 was analyzed in laser-induced subretinal inflammation in vivo. Quantification of laser-induced subretinal inflammation in wildtype- and $Tsp1^{-/-}$-mice at d7 that had been intravitreally injected with PBS, rHTRA1, rTSP1, and rHTRA1-digested rTSP1 at d3, reveal that (i) rHTRA1 aggravates subretinal inflammation in wildtype mice, but not in $Tsp1^{-/-}$-mice and that (ii) rTSP1, but not rHTRA1-digested rTSP1, significantly reduces this inflammation (FIG. 3C). Accordingly, associated choroidal neovascularization, measured as the surface covered by $CD102^-CNV$ on choroidal flatmounts at d7, underwent the same differences (FIG. 3D).

Taken together, these results show that HTRA1 digests TSP1, which results in a complete loss of function in terms of its anti-inflammatory effect in laser-induced inflammation in vivo.

Example 4

HTRA1 Cleaves TSP1 Between its Two VVM Sites that Activate CD47

To determine the HTRA1 cleavage sites of TSP1, the post-digestion fragments of TSP1 were submitted to liquid chromatography-tandem mass spectrometry. The analysis revealed that HTRA1 cleaved TSP1 at (i) a site known for its binding capacity to the integrin $\alpha3\beta1$, (ii) at two sites between the "type 2" domains and (iii) at two sites between the two valine-valine-methionine (VVM) sequences that can each interact with a CD47 receptor and are responsible for its highly efficient CD47 activation. The CD36 or LAP binding domains of TSP1 were not directly affected.

These results and the observation that TSP1 unfolds its immunosuppressive capacities via CD47 (FIG. 1) suggest that HTRA1 inactivates CD47 at least in part because its cleavage severs the two VVM sites of TSP1 apart. Indeed, the half maximal effective concentration (EC50) of TSP1 is much lower than the EC50 of CD47-activating peptides or TSP2, that only contains one VVM site.

Example 5

Activation of CD47 Reverses the Effect of HTRA1 on Subretinal Immunosuppressivity In Vitro To evaluate the effect of HTRA1 on subretinal immunosuppressivity, a co-culture model of CFSE labeled human monocytes and porcine RPE was developed. In this model and similar to in vivo adoptive transfer of mononuclear monocytes to the subretinal space (Levy et al., EMBO Mol Med. 2015, 7:211-226), at least 50% of the $CFSE^+$ monocytes are quickly eliminated, within 24 h, while RPE cell numbers (evidenced by counting of $OTX-2^+$nuclei) are not affected (FIGS. 4A and B). Recombinant HTRA1 (5 μg/mL) added to the co-culture, very significantly inhibited this immunosuppressive effect of the RPE and hMos were 3 to 4 times more numerous than in the control conditions at 24 h (p<0.0001 compared to the co-culture CTL group). The number of RPE cells in the co-culture counted automatically (Arrayscan) using OTX2 as a nuclear RPE-marker (see below) did not diminish significantly. Experiments using transwells showed that physical contact between RPE cells and Mos was required to induce Mo-death and heat-inactivation of HTRA1 abolished its effect (not shown).

To mimic the subretinal microenvironment observed in AML), the co-cultures were exposed to the presence of recombinant HTRA1 (5 μg/mL). The presence of the protease significantly disrupted the immunosuppressive effect (presumably by inactivating TSP1) of the RPE and monocytes survival was significantly increased (FIG. 4A, left panel). HTRA1 did not influence survival of RPE cells (FIG. 4A, right panel). In the attempt to reverse the HTRA1- induced TSP1 inactivation and disruption of the immunosuppressivity, the medium and the co-culture was treated for an additional 24 h with either PBS or a mixture of TSP1 (to activate CD47) and MegaFas1 (an agonist of FAS). At 48 h, the Mo-count in PBS treated HTRA1-exposed co-cultures remained significantly elevated compared to 48 h control conditions. However, the combined treatment of FAS and the CD47 agonist TSP1 eliminated a significant number of Mos and they were not significantly different to 48 h control cultures (FIG. 4B). Next, we tested whether the CD47-activating peptide PKt16 was able to accelerate Mo elimination in the HTRa1 co-culture condition. The CD47-activating peptide PKT16 (100 µM) or the 4NGG control peptide was added directly to HTRA1 treated co-culture. Quantification of CFSE+Monocytes reveal that 4NGG had no significant effect on monocytes number, but PKT16 completely reversed the HTRA1-induced increase in monocytes survival (FIG. 4C left panel). No toxicity of either 4NGG or PKT16 to RPE cells was observed (FIG. 4B right panel) as the number of OTX2+nuclei was unchanged. Furthermore, a dose response experiment revealed that 4N1K and PKT16, but not 4NNG, diminished the number of Mos (recognized by PU1 immunohistochemistry in these experiments, which avoids the CFSE staining) in HTRA1-activated co-cultures dose dependently at 48 h (FIG. 4D). Moreover, HTRA1-activated co-cultures were incubated with control peptide 4NGG, CD47-activating peptide 4N1K or 4N1K-GGGGGGGG-4N1K peptide (named d4N1K, Genepep) at various concentrations (0, 4, 20 and 50 µM). Quantification after 48 h of culture showed that the d4N1K that binds two CD47 receptors, similar to non-hydrolyzed TSP1, is significantly more effective to induce Mo elimination in the co-culture model (FIG. 4E).

Example 6

Activation of CD47 Accelerates Subretinal Mononuclear Phagocyte Elimination in Laser-Injured Inflammation Prone Cx3cr1$^{GFP/GFP}$ Mice In Vivo To evaluate the effect of CD47 activation in vivo, Cx3cr1$^{GFP/GFP}$ mice, that develop exaggerated subretinal inflammation with age, after a light-challenge and after laser injury (Combadière et al., JCI 2007; Levy et al., EMBO Mol Med. 2015) were submitted to a laser-injury. A volume of 2 µl of PBS, TSP1, a solution of the control peptide 4NGG or CD47-activating peptide PKT16 (100 µM) was injected at day 4 (when MP infiltration is maximal) and day 7 after the injury and evaluated subretinal inflammation on flatmounted RPE/choroidal flatmounts at day 10.

Results show that subretinal IBA-1$^+$MPs observed on the RPE adjacent to the laser impact were eliminated significantly more efficiently by ten days after a laser-impact, when TSP1 or PKT16 was injected compared to PBS or the control peptide 4NGG (FIG. 5).

Example 7

CD47 Activation Accelerates recMφ Elimination During Peritonitis

To test whether CD47 influences inflammation resolution in other pathological contexts, a model of acute thioglycollate-induced peritonitis was used, characterized by an early accumulation of neutrophils, followed by recruited monocyte-derived inflammatory macrophages (recMφ), both experiencing an apoptosis-driven elimination at different kinetics (Gautier et al., Blood. 2013, 122:2714-2722).

The proximity ligation assay revealed numerous and specific complexes CD11b and CD47 in WT recMφ retrieved at day 1 after induction of peritonitis (FIG. 6, top right, white dots marked by arrows). As a control, these complexes are not observed in CD47$^{-/-}$ mice (FIG. 6, bottom right).

The experiments also show that a single intra-peritoneal injection of recombinant TSP1 or the CD47-specific activating peptide PKHB1 at day 1 significantly accelerated the elimination of to recMφs as observed at day 2 (FIG. 7).

These results show that complexes of CD11b and CD47 are present on peritoneal recMφ and that CD47 activation accelerates recMφ elimination during peritonitis.

The invention claimed is:

1. A method for therapeutic treatment of retinal inflammation in a subject in need thereof, comprising administering to the subject an agent which activates CD47, wherein said agent directly activates CD47 and is selected from the group consisting of a modified TSP1 protein, wherein said TSP1 protein is resistant to the protease HTRA1, wherein the amino acid residues VT in position 242-243 of SEQ ID NO: 8 and/or the amino acid residues QV in position 288-289 of SEQ ID NO: 8 are deleted, or wherein the amino acid residue V in position 242 and/or the amino acid residue V in position 289 of SEQ ID NO: 8 is/are substituted; an activating peptide selected from 4N1K, PKHB1 and PKT16; and a multimeric peptide or polypeptide comprising at least two peptide monomers linked through a linker, wherein said at least two peptide monomers activate CD47 and are selected from the group consisting of 4N1K, PKHB1 and PKT16.

2. A method for therapeutic treatment of retinal inflammation in a subject in need thereof, comprising administering to the subject a composition comprising at least one agent which directly activates CD47 and which is selected from the group consisting of
   (i) A modified TSP1 protein, wherein said TSP1 protein is resistant to the protease HTRA1, wherein the amino acid residues VT in position 242-243 of SEQ ID NO: 8 and/or the amino acid residues QV in position 288-289 of SEQ ID NO: 8 are deleted, or wherein the amino acid residue V in position 242 and/or the amino acid residue V in position 289 of SEQ ID NO: 8 is/are substituted;
(ii) An activating peptide selected from 4N1K, PKHB1 and PKT16; and
(iii) A multimeric peptide or polypeptide comprising at least two peptide monomers linked through a linker, wherein said at least two peptide monomers activate CD47 and are selected from the group consisting of 4N1K, PKHB1 and PKT16; and
at least one agent which indirectly activates CD47 and which is selected from the group consisting of TSP1 activators, HTRA1 inhibitors and Fas activators.

3. The method according to claim 1, wherein said inflammation is associated with mononuclear phagocytes accumulation.

4. The method according to claim 1, wherein said retinal inflammation is selected from the group consisting of age-related macular degeneration, age-related maculopathy and retinitis pigmentosa.

5. The method according to claim 1, wherein said retinal inflammation is age-related macular degeneration.

\* \* \* \* \*

SEQUENCE LISTING

```
<160> NUMBER OF SEQ ID NOS: 14

<210> SEQ ID NO 1
<211> LENGTH: 10
<212> TYPE: PRT
<213> ORGANISM: Artificial Sequence
<220> FEATURE:
<223> OTHER INFORMATION: 4N1K peptide

<400> SEQUENCE: 1

Lys Arg Phe Tyr Val Val Met Trp Lys Lys
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Peptide linker

<400> SEQUENCE: 2

Gly Gly Gly Lys Gly Gly Gly Gly
1               5
```

<210> SEQ ID NO 3
<211> LENGTH: 8
<212> TYPE: PRT
<213> ORGANISM: Artificial Sequence
<220> FEATURE:
<223> OTHER INFORMATION: Peptide linker

<400> SEQUENCE: 3

Gly Gly Gly Asn Gly Ser Gly Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Peptide linker

<400> SEQUENCE: 4

Gly Gly Gly Cys Gly Gly Gly Gly
1               5

<210> SEQ ID NO 5
<211> LENGTH: 4
<212> TYPE: PRT
<213> ORGANISM: Artificial Sequence
<220> FEATURE:
<223> OTHER INFORMATION: Peptide linker

<400> SEQUENCE: 5

Gly Pro Asn Gly
1

<210> SEQ ID NO 6
<211> LENGTH: 8
<212> TYPE: PRT
<213> ORGANISM: Artificial Sequence
<220> FEATURE:
<223> OTHER INFORMATION: Peptide linker

<400> SEQUENCE: 6

Gly Gly Gly Gly Gly Gly Gly Gly
1               5

<210> SEQ ID NO 7
<211> LENGTH: 28
<212> TYPE: PRT
<213> ORGANISM: Artificial Sequence
<220> FEATURE:
<223> OTHER INFORMATION: 4N1K dimer

<400> SEQUENCE: 7

Lys Arg Phe Tyr Val Val Met Trp Lys Lys Gly Gly Gly Gly Gly
1               5                   10                  15
Gly Gly Lys Arg Phe Tyr Val Val Met Trp Lys Lys
            20                  25

<210> SEQ ID NO 8
<211> LENGTH: 369
<212> TYPE: PRT
<213> ORGANISM: Homo sapiens
<220> FEATURE:
<223> OTHER INFORMATION: TSP-1 C-terminal

<400> SEQUENCE: 8

Met Ala Cys Pro Gly Phe Leu Trp Ala Leu Val Ile Ser Thr Cys Leu

```
  1               5                  10                 15
Glu Phe Ser Met Ala Asp Tyr Lys Asp Asp Asp Lys Ala Leu Ala
                20                 25                 30
Asp Cys Cys Pro Leu Glu His Asn Pro Asp Gln Leu Asp Ser Asp Ser
        35                 40                 45
Asp Arg Ile Gly Asp Thr Cys Asp Asn Asn Gln Ile Asp Glu Asp
    50                 55                 60
Gly His Gln Asn Asn Leu Asp Asn Cys Pro Tyr Val Pro Asn Ala Asn
65                 70                 75                 80
Gln Ala Asp His Asp Lys Asp Gly Lys Gly Asp Ala Cys Asp His Asp
                85                 90                 95
Asp Asp Asn Asp Gly Ile Pro Asp Asp Lys Asp Asn Cys Arg Leu Val
            100                105                110
Pro Asn Pro Asp Gln Lys Asp Ser Asp Gly Asp Gly Arg Gly Asp Ala
            115                120                125
Cys Lys Asp Asp Phe Asp His Asp Ser Val Pro Asp Ile Asp Asp Ile
130                135                140
Cys Pro Glu Asn Val Asp Ile Ser Glu Thr Asp Phe Arg Arg Phe Gln
145                150                155                160
Met Ile Pro Leu Asp Pro Lys Gly Thr Ser Gln Asn Asp Pro Asn Trp
                165                170                175
Val Val Arg His Gln Gly Lys Glu Leu Val Gln Thr Val Asn Cys Asp
                180                185                190
Pro Gly Leu Ala Val Gly Tyr Asp Glu Phe Asn Ala Val Asp Phe Ser
            195                200                205
Gly Thr Phe Phe Ile Asn Thr Glu Arg Asp Asp Asp Tyr Ala Gly Phe
            210                215                220
Val Phe Gly Tyr Gln Ser Ser Arg Phe Tyr Val Val Met Trp Lys
225                230                235                240
Gln Val Thr Gln Ser Tyr Trp Asp Thr Asn Pro Thr Arg Ala Gln Gly
                245                250                255
Tyr Ser Gly Leu Ser Val Lys Val Val Asn Ser Thr Gly Pro Gly
                260                265                270
Glu His Leu Arg Asn Ala Leu Trp His Thr Gly Asn Thr Pro Gly Gln
            275                280                285
Val Arg Thr Leu Trp His Asp Pro Arg His Ile Gly Trp Lys Asp Phe
            290                295                300
Thr Ala Tyr Arg Trp Arg Leu Ser His Arg Pro Lys Thr Gly Phe Ile
305                310                315                320
Arg Val Val Met Tyr Glu Gly Lys Lys Ile Met Ala Asp Ser Gly Pro
                325                330                335
Ile Tyr Asp Lys Thr Tyr Ala Gly Gly Arg Leu Gly Leu Phe Val Phe
                340                345                350
Ser Gln Glu Met Val Phe Phe Ser Asp Leu Lys Tyr Glu Cys Arg Asp
            355                360                365
Pro
```

<210> SEQ ID NO 9
<211> LENGTH: 365
<212> TYPE: PRT
<213> ORGANISM: Artificial Sequence
<220> FEATURE:
<223> OTHER INFORMATION: Modified TSP-1 C-terminal

<400> SEQUENCE: 9

```
Met Ala Cys Pro Gly Phe Leu Trp Ala Leu Val Ile Ser Thr Cys Leu
1               5                   10                  15

Glu Phe Ser Met Ala Asp Tyr Lys Asp Asp Asp Lys Ala Leu Cys
            20                  25                  30

Asp Asn Cys Pro Leu Glu His Asn Pro Asp Gln Leu Asp Ser Asp Ser
        35                  40                  45

Asp Arg Ile Gly Asp Thr Cys Asp Asn Asn Gln Asp Ile Asp Glu Asp
    50                  55                  60

Gly His Gln Asn Asn Leu Asp Asn Cys Pro Tyr Val Pro Asn Ala Asn
65                  70                  75                  80

Gln Ala Asp His Asp Lys Asp Gly Lys Gly Asp Ala Cys Asp His Asp
            85                  90                  95

Asp Asp Asn Asp Gly Ile Pro Asp Asp Lys Asp Asn Cys Arg Leu Val
        100                 105                 110

Pro Asn Pro Asp Gln Lys Asp Ser Asp Gly Asp Gly Arg Gly Asp Ala
    115                 120                 125

Cys Lys Asp Asp Phe Asp His Asp Ser Val Pro Asp Ile Asp Asp Ile
130                 135                 140

Cys Pro Glu Asn Val Asp Ile Ser Glu Thr Asp Phe Arg Arg Phe Gln
145                 150                 155                 160

Met Ile Pro Leu Asp Pro Lys Gly Thr Ser Gln Asn Asp Pro Asn Trp
            165                 170                 175

Val Val Arg His Gln Gly Lys Glu Leu Val Gln Thr Val Asn Cys Asp
        180                 185                 190

Pro Gly Leu Ala Val Gly Tyr Asp Glu Phe Asn Ala Val Asp Phe Ser
    195                 200                 205

Gly Thr Phe Phe Ile Asn Thr Glu Arg Asp Asp Asp Tyr Ala Gly Phe
210                 215                 220

Val Phe Gly Tyr Gln Ser Ser Arg Phe Tyr Val Val Met Trp Lys
225                 230                 235                 240

Gln Gln Ser Tyr Trp Asp Thr Asn Pro Thr Arg Ala Gln Gly Tyr Ser
            245                 250                 255

Gly Leu Ser Val Lys Val Val Asn Ser Thr Thr Gly Pro Gly Glu His
        260                 265                 270

Leu Arg Asn Ala Leu Trp His Thr Gly Asn Thr Pro Gly Arg Thr Leu
    275                 280                 285

Trp His Asp Pro Arg His Ile Gly Trp Lys Asp Phe Thr Ala Tyr Arg
290                 295                 300

Trp Arg Leu Ser His Arg Pro Lys Thr Gly Phe Ile Arg Val Val Met
305                 310                 315                 320

Tyr Glu Gly Lys Lys Ile Met Ala Asp Ser Gly Pro Ile Tyr Asp Lys
            325                 330                 335

Thr Tyr Ala Gly Gly Arg Leu Gly Leu Phe Val Phe Ser Gln Glu Met
        340                 345                 350

Val Phe Phe Ser Asp Leu Lys Tyr Glu Cys Arg Asp Pro
    355                 360                 365

<210> SEQ ID NO 10
<211> LENGTH: 365
<212> TYPE: PRT
<213> ORGANISM: Artificial Sequence
<220> FEATURE:
<223> OTHER INFORMATION: Modified TSP-1 C-terminal

<400> SEQUENCE: 10
```

```
Met Ala Cys Pro Gly Phe Leu Trp Ala Leu Val Ile Ser Thr Cys Leu
1               5                   10                  15

Glu Phe Ser Met Ala Asp Tyr Lys Asp Asp Asp Lys Ala Leu Ala
            20                  25                  30

Asp Asn Cys Pro Leu Glu His Asn Pro Asp Gln Leu Asp Ser Asp Ser
        35                  40                  45

Asp Arg Ile Gly Asp Thr Cys Asp Asn Asn Gln Asp Ile Asp Glu Asp
    50                  55                  60

Gly His Gln Asn Asn Leu Asp Asn Cys Pro Tyr Val Pro Asn Ala Asn
65                  70                  75                  80

Gln Ala Asp His Asp Lys Asp Gly Lys Gly Asp Ala Cys Asp His Asp
            85                  90                  95

Asp Asp Asn Asp Gly Ile Pro Asp Asp Lys Asp Asn Cys Arg Leu Val
            100                 105                 110

Pro Asn Pro Asp Gln Lys Asp Ser Asp Gly Asp Gly Arg Gly Asp Ala
        115                 120                 125

Cys Lys Asp Asp Phe Asp His Asp Ser Val Pro Asp Ile Asp Asp Ile
        130                 135                 140

Cys Pro Glu Asn Val Asp Ile Ser Glu Thr Asp Phe Arg Arg Phe Gln
145                 150                 155                 160

Met Ile Pro Leu Asp Pro Lys Gly Thr Ser Gln Asn Asp Pro Asn Trp
            165                 170                 175

Val Val Arg His Gln Gly Lys Glu Leu Val Gln Thr Val Asn Ser Asp
            180                 185                 190

Pro Gly Leu Ala Val Gly Tyr Asp Glu Phe Asn Ala Val Asp Phe Ser
        195                 200                 205

Gly Thr Phe Phe Ile Asn Thr Glu Arg Asp Asp Asp Tyr Ala Gly Phe
210                 215                 220

Val Phe Gly Tyr Gln Ser Ser Ser Arg Phe Tyr Val Val Met Trp Lys
225                 230                 235                 240

Gln Gln Ser Tyr Trp Asp Thr Asn Pro Thr Arg Ala Gln Gly Tyr Ser
            245                 250                 255

Gly Leu Ser Val Lys Val Val Lys Ser Thr Thr Gly Pro Gly Glu His
            260                 265                 270

Leu Arg Asn Ala Leu Trp His Thr Gly Asn Thr Pro Gly Arg Thr Leu
        275                 280                 285

Trp His Asp Pro Arg His Ile Gly Trp Lys Asp Phe Thr Ala Tyr Arg
290                 295                 300

Trp Arg Leu Ser His Arg Pro Lys Thr Gly Phe Ile Arg Val Val Met
305                 310                 315                 320

Tyr Glu Gly Lys Lys Ile Met Ala Asp Ser Gly Pro Ile Tyr Asp Lys
            325                 330                 335

Thr Tyr Ala Gly Gly Arg Leu Gly Leu Phe Val Phe Ser Gln Glu Met
            340                 345                 350

Val Phe Phe Ser Asp Leu Lys Tyr Glu Cys Arg Asp Pro
            355                 360                 365

<210> SEQ ID NO 11
<211> LENGTH: 369
<212> TYPE: PRT
<213> ORGANISM: Artificial Sequence
<220> FEATURE:
<223> OTHER INFORMATION: Modified TSP-1 C-terminal

<400> SEQUENCE: 11
```

```
Met Ala Cys Pro Gly Phe Leu Trp Ala Leu Val Ile Ser Thr Cys Leu
1               5                   10                  15

Glu Phe Ser Met Ala Asp Tyr Lys Asp Asp Asp Lys Ala Leu Cys
            20                  25                  30

Asp Asn Cys Pro Leu Glu His Asn Pro Asp Gln Leu Asp Ser Asp Ser
        35                  40                  45

Asp Arg Ile Gly Asp Thr Cys Asp Asn Asn Gln Asp Ile Asp Glu Asp
        50                  55                  60

Gly His Gln Asn Asn Leu Asp Asn Cys Pro Tyr Val Pro Asn Ala Asn
65                  70                  75                  80

Gln Ala Asp His Asp Lys Asp Gly Lys Gly Asp Ala Cys Asp His Asp
            85                  90                  95

Asp Asp Asn Asp Gly Ile Pro Asp Asp Lys Asp Asn Cys Arg Leu Val
            100                 105                 110

Pro Asn Pro Asp Gln Lys Asp Ser Asp Gly Asp Gly Arg Gly Asp Ala
            115                 120                 125

Cys Lys Asp Asp Phe Asp His Asp Ser Val Pro Asp Ile Asp Asp Ile
130                 135                 140

Cys Pro Glu Asn Val Asp Ile Ser Glu Thr Asp Phe Arg Arg Phe Gln
145                 150                 155                 160

Met Ile Pro Leu Asp Pro Lys Gly Thr Ser Gln Asn Asp Pro Asn Trp
            165                 170                 175

Val Val Arg His Gln Gly Lys Glu Leu Val Gln Thr Val Asn Cys Asp
            180                 185                 190

Pro Gly Leu Ala Val Gly Tyr Asp Glu Phe Asn Ala Val Asp Phe Ser
            195                 200                 205

Gly Thr Phe Phe Ile Asn Thr Glu Arg Asp Asp Asp Tyr Ala Gly Phe
            210                 215                 220

Val Phe Gly Tyr Gln Ser Ser Arg Phe Tyr Val Val Met Trp Lys
225                 230                 235                 240

Gln Asn Thr Gln Ser Tyr Trp Asp Thr Asn Pro Thr Arg Ala Gln Gly
            245                 250                 255

Tyr Ser Gly Leu Ser Val Lys Val Val Asn Ser Thr Thr Gly Pro Gly
            260                 265                 270

Glu His Leu Arg Asn Ala Leu Trp His Thr Gly Asn Thr Pro Gly Gln
            275                 280                 285

Asn Arg Thr Leu Trp His Asp Pro Arg His Ile Gly Trp Lys Asp Phe
            290                 295                 300

Thr Ala Tyr Arg Trp Arg Leu Ser His Arg Pro Lys Thr Gly Phe Ile
305                 310                 315                 320

Arg Val Val Met Tyr Glu Gly Lys Lys Ile Met Ala Asp Ser Gly Pro
            325                 330                 335

Ile Tyr Asp Lys Thr Tyr Ala Gly Gly Arg Leu Gly Leu Phe Val Phe
            340                 345                 350

Ser Gln Glu Met Val Phe Phe Ser Asp Leu Lys Tyr Glu Cys Arg Asp
            355                 360                 365

Pro
```

<210> SEQ ID NO 12
<211> LENGTH: 369
<212> TYPE: PRT
<213> ORGANISM: Artificial Sequence
<220> FEATURE:
<223> OTHER INFORMATION: Modified TSP-1 C-terminal

<400> SEQUENCE: 12

```
Met Ala Cys Pro Gly Phe Leu Trp Ala Leu Val Ile Ser Thr Cys Leu
1               5                   10                  15

Glu Phe Ser Met Ala Asp Tyr Lys Asp Asp Asp Lys Ala Leu Ala
            20                  25                  30

Asp Asn Cys Pro Leu Glu His Asn Pro Asp Gln Leu Asp Ser Asp Ser
            35                  40                  45

Asp Arg Ile Gly Asp Thr Cys Asp Asn Asn Gln Ile Asp Glu Asp
        50                  55                  60

Gly His Gln Asn Asn Leu Asp Asn Cys Pro Tyr Val Pro Asn Ala Asn
65                  70                  75                  80

Gln Ala Asp His Asp Lys Asp Gly Lys Gly Asp Ala Cys Asp His Asp
                85                  90                  95

Asp Asp Asn Asp Gly Ile Pro Asp Asp Lys Asp Asn Cys Arg Leu Val
                100                 105                 110

Pro Asn Pro Asp Gln Lys Asp Ser Asp Gly Asp Gly Arg Gly Asp Ala
            115                 120                 125

Cys Lys Asp Asp Phe Asp His Asp Ser Val Pro Asp Ile Asp Asp Ile
130                 135                 140

Cys Pro Glu Asn Val Asp Ile Ser Glu Thr Asp Phe Arg Arg Phe Gln
145                 150                 155                 160

Met Ile Pro Leu Asp Pro Lys Gly Thr Ser Gln Asn Asp Pro Asn Trp
                165                 170                 175

Val Val Arg His Gln Gly Lys Glu Leu Val Gln Thr Val Asn Ser Asp
            180                 185                 190

Pro Gly Leu Ala Val Gly Tyr Asp Glu Phe Asn Ala Val Asp Phe Ser
        195                 200                 205

Gly Thr Phe Phe Ile Asn Thr Glu Arg Asp Asp Asp Tyr Ala Gly Phe
        210                 215                 220

Val Phe Gly Tyr Gln Ser Ser Ser Arg Phe Tyr Val Val Met Trp Lys
225                 230                 235                 240

Gln Asn Thr Gln Ser Tyr Trp Asp Thr Asn Pro Thr Arg Ala Gln Gly
                245                 250                 255

Tyr Ser Gly Leu Ser Val Lys Val Val Lys Ser Thr Gly Pro Gly
            260                 265                 270

Glu His Leu Arg Asn Ala Leu Trp His Thr Gly Asn Thr Pro Gly Gln
            275                 280                 285

Asn Arg Thr Leu Trp His Asp Pro Arg His Ile Gly Trp Lys Asp Phe
            290                 295                 300

Thr Ala Tyr Arg Trp Arg Leu Ser His Arg Pro Lys Thr Gly Phe Ile
305                 310                 315                 320

Arg Val Val Met Tyr Glu Gly Lys Lys Ile Met Ala Asp Ser Gly Pro
                325                 330                 335

Ile Tyr Asp Lys Thr Tyr Ala Gly Gly Arg Leu Gly Leu Phe Val Phe
            340                 345                 350

Ser Gln Glu Met Val Phe Phe Ser Asp Leu Lys Tyr Glu Cys Arg Asp
            355                 360                 365

Pro
```

<210> SEQ ID NO 13
<211> LENGTH: 1168
<212> TYPE: PRT
<213> ORGANISM: Artificial Sequence -continued
<220> FEATURE:
<223> OTHER INFORMATION: HTRA1-resistant modified TSP1

<400> SEQUENCE: 13

```
Leu Ala Trp Gly Leu Gly Val Leu Phe Leu Met His Val Cys Gly Thr
1               5                   10                  15

Asn Arg Ile Pro Glu Ser Gly Gly Asp Asn Ser Val Phe Asp Ile Phe
            20                  25                  30

Glu Leu Thr Gly Ala Ala Arg Lys Gly Ser Gly Arg Arg Leu Val Lys
        35                  40                  45

Gly Pro Asp Pro Ser Ser Pro Ala Phe Arg Ile Glu Asp Ala Asn Leu
    50                  55                  60

Ile Pro Pro Val Pro Asp Asp Lys Phe Gln Asp Leu Val Asp Ala Val
65                  70                  75                  80

Arg Ala Glu Lys Gly Phe Leu Leu Leu Ala Ser Leu Arg Gln Met Lys
                85                  90                  95

Lys Thr Arg Gly Thr Leu Leu Ala Leu Glu Arg Lys Asp His Ser Gly
            100                 105                 110

Gln Val Phe Ser Val Val Ser Asn Gly Lys Ala Gly Thr Leu Asp Leu
        115                 120                 125

Ser Leu Thr Val Gln Gly Lys Gln His Val Val Ser Val Glu Glu Ala
    130                 135                 140

Leu Leu Ala Thr Gly Gln Trp Lys Ser Ile Thr Leu Phe Val Gln Glu
145                 150                 155                 160

Asp Arg Ala Gln Leu Tyr Ile Asp Cys Glu Lys Met Glu Asn Ala Glu
                165                 170                 175

Leu Asp Val Pro Ile Gln Ser Val Phe Thr Arg Asp Leu Ala Ser Lys
            180                 185                 190

Ser Arg Met Tyr Val Ala Lys Gly Ser Ala Arg Glu Ser His Phe Arg
        195                 200                 205

Gly Leu Leu Gln Asn Val His Leu Val Phe Glu Asn Ser Val Glu Asp
    210                 215                 220

Ile Leu Ser Lys Lys Gly Cys Gln Gln Gly Thr Ser Val Leu Leu Thr
225                 230                 235                 240

Leu Asp Asn Asn Val Val Asn Gly Ser Ser Pro Ala Ile Arg Thr Asn
                245                 250                 255

Tyr Ile Gly His Lys Thr Lys Asp Leu Gln Ala Ile Cys Gly Ile Ser
            260                 265                 270

Cys Asp Glu Leu Ser Ser Met Val Leu Glu Leu Arg Gly Leu Arg Thr
        275                 280                 285

Ile Val Thr Thr Leu Gln Asp Ser Ile Arg Lys Val Thr Glu Glu Asn
    290                 295                 300

Lys Glu Leu Ala Asn Glu Leu Arg Arg Pro Pro Leu Cys Tyr His Asn
305                 310                 315                 320

Gly Val Gln Tyr Arg Asn Asn Glu Glu Trp Thr Val Asp Ser Cys Thr
                325                 330                 335

Glu Cys His Cys Gln Asn Ser Val Thr Ile Cys Lys Lys Val Ser Cys
            340                 345                 350

Pro Ile Met Pro Cys Ser Asn Ala Thr Val Pro Asp Gly Glu Cys Cys
        355                 360                 365

Pro Arg Cys Trp Pro Ser Asp Ser Ala Asp Asp Gly Trp Ser Pro Trp
    370                 375                 380

Ser Glu Trp Thr Ser Cys Ser Thr Ser Cys Gly Asn Gly Ile Gln Gln
385                 390                 395                 400

-continued

Arg Gly Arg Ser Cys Asp Ser Leu Asn Asn Arg Cys Leu Gly Pro Ser
            405                 410                 415

Ile Gln Thr Arg Ala Cys Ser Leu Ser Lys Cys Asp Thr Arg Ile Arg
            420                 425                 430

Gln Asp Gly Gly Trp Ser His Trp Ser Pro Trp Ser Ser Cys Ser Val
            435                 440                 445

Thr Cys Gly Asp Gly Val Ile Thr Arg Ile Arg Leu Cys Asn Ser Pro
            450                 455                 460

Ser Pro Gln Met Asn Gly Lys Pro Cys Glu Gly Glu Ala Arg Glu Thr
465                 470                 475                 480

Lys Ala Cys Lys Lys Asp Ala Cys Pro Ile Asn Gly Gly Trp Gly Pro
            485                 490                 495

Trp Ser Pro Trp Asp Ile Cys Ser Val Thr Cys Gly Gly Gly Val Gln
            500                 505                 510

Lys Arg Ser Arg Leu Cys Asn Asn Pro Thr Pro Gln Phe Gly Gly Lys
            515                 520                 525

Asp Cys Val Gly Asp Val Thr Glu Asn Gln Ile Cys Asn Lys Gln Asp
            530                 535                 540

Cys Pro Ile Asp Gly Cys Leu Ser Asn Pro Cys Phe Ala Gly Val Lys
545                 550                 555                 560

Cys Thr Ser Tyr Pro Asp Gly Ser Trp Lys Cys Gly Ala Cys Pro Pro
            565                 570                 575

Gly Tyr Ser Gly Asn Gly Ile Gln Cys Thr Asp Val Asp Glu Cys Lys
            580                 585                 590

Glu Val Pro Asp Ala Cys Phe Asn His Asn Gly Glu His Arg Cys Glu
            595                 600                 605

Asn Thr Asp Pro Gly Tyr Asn Cys Leu Pro Cys Pro Pro Arg Tyr Arg
            610                 615                 620

Gly Asn Gln Pro Val Gly Val Gly Leu Glu Ala Ala Lys Thr Glu Lys
625                 630                 635                 640

Gln Val Cys Glu Pro Glu Asn Pro Cys Lys Asp Gly Thr His Asp Cys
            645                 650                 655

Asn Lys Asn Ala Lys Cys Asn Tyr Leu Gly His Tyr Ser Asp Pro Met
            660                 665                 670

Tyr Arg Cys Glu Cys Lys Pro Gly Tyr Ala Gly Asn Gly Ile Ile Cys
            675                 680                 685

Gly Glu Asp Thr Asp Leu Asp Gly Trp Pro Asn Glu Asn Leu Val Cys
            690                 695                 700

Val Ala Asn Ala Thr Tyr His Cys Lys Lys Asp Asn Cys Pro Asn Leu
705                 710                 715                 720

Pro Asn Ser Gly Gln Glu Asp Tyr Asp Lys Asp Gly Ile Gly Asp Ala
            725                 730                 735

Cys Asp Asp Asp Asp Asp Asn Asp Lys Ile Pro Asp Asp Arg Asp Asn
            740                 745                 750

Cys Pro Phe His Tyr Asn Pro Ala Gln Tyr Asp Tyr Asp Arg Asp Asp
            755                 760                 765

Val Gly Asp Arg Cys Asp Asn Cys Pro Tyr Asn His Asn Pro Asp Gln
            770                 775                 780

Ala Asp Thr Asp Asn Asn Gly Glu Gly Asp Ala Cys Ala Ala Asp Ile
785                 790                 795                 800

Asp Gly Asp Gly Ile Leu Asn Glu Arg Asp Asn Cys Gln Tyr Val Tyr
            805                 810                 815

```
Asn Val Asp Gln Arg Asp Thr Asp Met Asp Gly Val Gly Asp Gln Cys
                820                 825                 830

Asp Asn Cys Pro Leu Glu His Asn Pro Asp Gln Leu Asp Ser Asp Ser
            835                 840                 845

Asp Arg Ile Gly Asp Thr Cys Asp Asn Asn Gln Asp Ile Asp Glu Asp
        850                 855                 860

Gly His Gln Asn Asn Leu Asp Asn Cys Pro Tyr Val Pro Asn Ala Asn
865                 870                 875                 880

Gln Ala Asp His Asp Lys Asp Gly Lys Gly Asp Ala Cys Asp His Asp
                885                 890                 895

Asp Asp Asn Asp Gly Ile Pro Asp Lys Asp Asn Cys Arg Leu Val
            900                 905                 910

Pro Asn Pro Asp Gln Lys Asp Ser Asp Gly Asp Gly Arg Gly Asp Ala
        915                 920                 925

Cys Lys Asp Asp Phe Asp His Asp Ser Val Pro Asp Ile Asp Asp Ile
930                 935                 940

Cys Pro Glu Asn Val Asp Ile Ser Glu Thr Asp Phe Arg Arg Phe Gln
945                 950                 955                 960

Met Ile Pro Leu Asp Pro Lys Gly Thr Ser Gln Asn Asp Pro Asn Trp
                965                 970                 975

Val Val Arg His Gln Gly Lys Glu Leu Val Gln Thr Val Asn Cys Asp
            980                 985                 990

Pro Gly Leu Ala Val Gly Tyr Asp Glu Phe Asn Ala Val Asp Phe Ser
        995                 1000                1005

Gly Thr Phe Phe Ile Asn Thr Glu Arg Asp Asp Asp Tyr Ala Gly Phe
    1010                1015                1020

Val Phe Gly Tyr Gln Ser Ser Ser Arg Phe Tyr Val Val Met Trp Lys
1025                1030                1035                1040

Gln Val Thr Gln Thr Tyr Trp Glu Asp Gln Pro Thr Arg Ala Tyr Gly
                1045                1050                1055

Tyr Ser Gly Val Ser Leu Lys Val Val Asn Ser Thr Thr Gly Thr Gly
            1060                1065                1070

Glu His Leu Arg Asn Ala Leu Trp His Thr Gly Asn Thr Pro Gly Gln
        1075                1080                1085

Val Arg Thr Leu Trp His Asp Pro Arg Asn Ile Gly Trp Lys Asp Tyr
    1090                1095                1100

Thr Ala Tyr Arg Trp His Leu Thr His Arg Pro Lys Thr Gly Tyr Ile
1105                1110                1115                1120

Arg Val Val Met Tyr Glu Gly Lys Lys Ile Met Ala Asp Ser Gly Pro
                1125                1130                1135

Ile Tyr Asp Lys Thr Tyr Ala Gly Gly Arg Leu Gly Leu Phe Val Phe
            1140                1145                1150

Ser Gln Glu Met Val Phe Phe Ser Asp Leu Lys Tyr Glu Cys Arg Asp
        1155                1160                1165

<210> SEQ ID NO 14
<211> LENGTH: 1171
<212> TYPE: PRT
<213> ORGANISM: Artificial Sequence
<220> FEATURE:
<223> OTHER INFORMATION: HTRA1-resistant derived TSP2

<400> SEQUENCE: 14

Met Val Trp Arg Leu Val Leu Leu Ala Leu Trp Val Trp Pro Ser Thr
1

-continued

Gln Ala Gly His Gln Asp Lys Asp Thr Thr Phe Asp Leu Phe Ser Ile
            20                  25                  30

Ser Asn Ile Asn Arg Lys Thr Ile Gly Ala Lys Gln Phe Arg Gly Pro
        35                  40                  45

Asp Pro Gly Val Pro Ala Tyr Arg Phe Val Arg Phe Asp Tyr Ile Pro
    50                  55                  60

Pro Val Asn Ala Asp Asp Leu Ser Lys Ile Thr Lys Ile Met Arg Gln
65                  70                  75                  80

Lys Glu Gly Phe Phe Leu Thr Ala Gln Leu Lys Gln Asp Gly Lys Ser
                85                  90                  95

Arg Gly Thr Leu Leu Ala Leu Glu Gly Pro Gly Leu Ser Gln Arg Gln
            100                 105                 110

Phe Glu Ile Val Ser Asn Gly Pro Ala Asp Thr Leu Asp Leu Thr Tyr
        115                 120                 125

Trp Ile Asp Gly Thr Arg His Val Ser Leu Glu Asp Val Gly Leu
    130                 135                 140

Ala Asp Ser Gln Trp Lys Asn Val Thr Val Gln Val Ala Gly Glu Thr
145                 150                 155                 160

Tyr Ser Leu His Val Gly Cys Asp Leu Ile Asp Ser Phe Ala Leu Asp
            165                 170                 175

Glu Pro Phe Tyr Glu His Leu Gln Ala Glu Lys Ser Arg Met Tyr Val
        180                 185                 190

Ala Lys Gly Ser Ala Arg Glu Ser His Phe Arg Gly Leu Leu Gln Asn
    195                 200                 205

Val His Leu Val Phe Glu Asn Ser Val Glu Asp Ile Leu Ser Lys Lys
210                 215                 220

Gly Cys Gln Gln Gly Gln Gly Ala Glu Ile Asn Ala Ile Ser Glu Asn
225                 230                 235                 240

Thr Glu Thr Leu Arg Leu Gly Pro His Val Thr Thr Glu Tyr Val Gly
            245                 250                 255

Pro Ser Ser Glu Arg Arg Pro Glu Val Cys Glu Arg Ser Cys Glu Glu
        260                 265                 270

Leu Gly Asn Met Val Gln Glu Leu Ser Gly Leu His Val Leu Val Asn
    275                 280                 285

Gln Leu Ser Glu Asn Leu Lys Arg Val Ser Asn Asp Asn Gln Phe Leu
290                 295                 300

Trp Glu Leu Ile Gly Gly Pro Pro Lys Thr Arg Asn Met Ser Ala Cys
305                 310                 315                 320

Trp Gln Asp Gly Arg Phe Phe Ala Glu Asn Glu Thr Trp Val Val Asp
            325                 330                 335

Ser Cys Thr Thr Cys Thr Cys Lys Lys Phe Lys Thr Ile Cys His Gln
        340                 345                 350

Ile Thr Cys Pro Pro Ala Thr Cys Ala Ser Pro Ser Phe Val Glu Gly
    355                 360                 365

Glu Cys Cys Pro Ser Cys Leu His Ser Val Asp Gly Glu Glu Gly Trp
370                 375                 380

Ser Pro Trp Ala Glu Trp Thr Gln Cys Ser Val Thr Cys Gly Ser Gly
385                 390                 395                 400

Thr Gln Gln Arg Gly Arg Ser Cys Asp Val Thr Ser Asn Thr Cys Leu
            405                 410                 415

Gly Pro Ser Ile Gln Thr Arg Ala Cys Ser Leu Ser Lys Cys Asp Thr
        420                 425                 430

Arg Ile Arg Gln Asp Gly Gly Trp Ser His Trp Ser Pro Trp Ser Ser

-continued

```
            435                 440                 445
Cys Ser Val Thr Cys Gly Val Gly Asn Ile Thr Arg Ile Arg Leu Cys
450                 455                 460

Asn Ser Pro Val Pro Gln Met Gly Gly Lys Asn Cys Lys Gly Ser Gly
465                 470                 475                 480

Arg Glu Thr Lys Ala Cys Gln Gly Ala Pro Cys Pro Ile Asp Gly Arg
                485                 490                 495

Trp Ser Pro Trp Ser Pro Trp Ser Ala Cys Thr Val Thr Cys Ala Gly
                500                 505                 510

Gly Ile Arg Glu Arg Thr Arg Val Cys Asn Ser Pro Glu Pro Gln Tyr
                515                 520                 525

Gly Gly Lys Ala Cys Val Gly Asp Val Gln Glu Arg Gln Met Cys Asn
530                 535                 540

Lys Arg Ser Cys Pro Val Asp Gly Cys Leu Ser Asn Pro Cys Phe Pro
545                 550                 555                 560

Gly Ala Gln Cys Ser Ser Phe Pro Asp Gly Ser Trp Ser Cys Gly Ser
                565                 570                 575

Cys Pro Val Gly Phe Leu Gly Asn Gly Thr His Cys Glu Asp Leu Asp
                580                 585                 590

Glu Cys Ala Leu Val Pro Asp Ile Cys Phe Ser Thr Ser Lys Val Pro
                595                 600                 605

Arg Cys Val Asn Thr Gln Pro Gly Phe His Cys Leu Pro Cys Pro Pro
610                 615                 620

Arg Tyr Arg Gly Asn Gln Pro Val Gly Val Gly Leu Glu Ala Ala Lys
625                 630                 635                 640

Thr Glu Lys Gln Val Cys Glu Pro Glu Asn Pro Cys Lys Asp Lys Thr
                645                 650                 655

His Asn Cys His Lys His Ala Glu Cys Ile Tyr Leu Gly His Phe Ser
                660                 665                 670

Asp Pro Met Tyr Lys Cys Glu Cys Gln Thr Gly Tyr Ala Gly Asp Gly
                675                 680                 685

Leu Ile Cys Gly Glu Asp Ser Asp Leu Asp Gly Trp Pro Asn Leu Asn
                690                 695                 700

Leu Val Cys Ala Thr Asn Ala Thr Tyr His Cys Ile Lys Asp Asn Cys
705                 710                 715                 720

Pro His Leu Pro Asn Ser Gly Gln Glu Asp Phe Asp Lys Asp Gly Ile
                725                 730                 735

Gly Asp Ala Cys Asp Asp Asp Asp Asn Asp Gly Val Thr Asp Glu
                740                 745                 750

Lys Asp Asn Cys Gln Leu Leu Phe Asn Pro Arg Gln Ala Asp Tyr Asp
                755                 760                 765

Lys Asp Glu Val Gly Asp Arg Cys Asp Asn Cys Pro Tyr Val His Asn
                770                 775                 780

Pro Ala Gln Ile Asp Thr Asp Asn Asn Gly Glu Gly Asp Ala Cys Ser
785                 790                 795                 800

Val Asp Ile Asp Gly Asp Asp Val Phe Asn Glu Arg Asp Asn Cys Pro
                805                 810                 815

Tyr Val Tyr Asn Thr Asp Gln Arg Asp Thr Asp Gly Asp Gly Val Gly
                820                 825                 830

Asp His Cys Asp Asn Cys Pro Leu Val His Asn Pro Asp Gln Thr Asp
                835                 840                 845

Val Asp Asn Asp Leu Val Gly Asp Gln Cys Asp Asn Asn Glu Asp Ile
850                 855                 860
```

```
Asp Asp Asp Gly His Gln Asn Gln Asp Asn Cys Pro Tyr Ile Ser
865                 870                 875                 880

Asn Ala Asn Gln Ala Asp His Asp Arg Asp Gly Gln Gly Asp Ala Cys
                885                 890                 895

Asp Pro Asp Asp Asn Asp Gly Val Pro Asp Arg Asp Asn Cys
        900                 905                 910

Arg Leu Val Phe Asn Pro Asp Gln Glu Asp Leu Asp Gly Asp Gly Arg
        915                 920                 925

Gly Asp Ile Cys Lys Asp Asp Phe Asp Asn Asp Asn Ile Pro Asp Ile
        930                 935                 940

Asp Asp Val Cys Pro Glu Asn Asn Ala Ile Ser Glu Thr Asp Phe Arg
945                 950                 955                 960

Asn Phe Gln Met Val Pro Leu Asp Pro Lys Gly Thr Thr Gln Ile Asp
                965                 970                 975

Pro Asn Trp Val Ile Arg His Gln Gly Lys Glu Leu Val Gln Thr Ala
            980                 985                 990

Asn Ser Asp Pro Gly Ile Ala Val Gly Phe Asp Glu Phe Gly Ser Val
        995                 1000                1005

Asp Phe Ser Gly Thr Phe Tyr Val Asn Thr Asp Arg Asp Asp Asp Tyr
        1010                1015                1020

Ala Gly Phe Val Phe Gly Tyr Gln Ser Ser Ser Arg Phe Tyr Val Val
1025                1030                1035                1040

Met Trp Lys Gln Val Thr Gln Thr Tyr Trp Glu Asp Gln Pro Thr Arg
                1045                1050                1055

Ala Tyr Gly Tyr Ser Gly Val Ser Leu Lys Val Val Asn Ser Thr Thr
            1060                1065                1070

Gly Thr Gly Glu His Leu Arg Asn Ala Leu Trp His Thr Gly Asn Thr
        1075                1080                1085

Pro Gly Gln Val Arg Thr Leu Trp His Asp Pro Arg Asn Ile Gly Trp
        1090                1095                1100

Lys Asp Tyr Thr Ala Tyr Arg Trp His Leu Thr His Arg Pro Lys Thr
1105                1110                1115                1120

Gly Phe Ile Arg Val Val Met Tyr Glu Gly Lys Lys Ile Met Ala Asp
                1125                1130                1135

Ser Gly Pro Ile Tyr Asp Lys Thr Tyr Ala Gly Gly Arg Leu Gly Leu
            1140                1145                1150

Phe Val Phe Ser Gln Glu Met Val Phe Phe Ser Asp Leu Lys Tyr Glu
            1155                1160                1165

Cys Arg Asp
1170
```